US006787333B2

(12) United States Patent
Callahan et al.

(10) Patent No.: US 6,787,333 B2
(45) Date of Patent: Sep. 7, 2004

(54) RETROVIRUS ISOLATED FROM HUMANS

(75) Inventors: Margaret E. Callahan, Decatur, GA (US); Thomas M. Folks, Snellville, GA (US); Paul Sandstrom, Kanata (CA); Shambavi Subbarao, Doraville, GA (US); Jennifer Brown, Sacramento, CA (US); Walid Heneine, Atlanta, GA (US); William M. Switzer, Stone Mountain, GA (US)

(73) Assignee: The United States of America as represented by the Department of Health and Human Services, Washington, DC (US)

( * ) Notice: Subject to any disclaimer, the term of this patent is extended or adjusted under 35 U.S.C. 154(b) by 0 days.

(21) Appl. No.: 10/272,394

(22) Filed: Oct. 15, 2002

(65) Prior Publication Data

US 2003/0148509 A1 Aug. 7, 2003

Related U.S. Application Data

(60) Division of application No. 09/692,652, filed on Oct. 19, 2000, now Pat. No. 6,492,165, which is a continuation-in-part of application No. 09/367,213, filed as application No. PCT/US98/02598 on Feb. 12, 1998, now abandoned, which is a continuation-in-part of application No. 08/798,071, filed on Feb. 12, 1997, now Pat. No. 5,882,912.

(51) Int. Cl.[7] .............................. C12Q 1/06; C12Q 1/70; C12Q 1/68
(52) U.S. Cl. .................................. 435/39; 435/5; 435/6
(58) Field of Search .................................. 435/5, 6, 39

(56) References Cited

U.S. PATENT DOCUMENTS 5,108,920 A   4/1992   Ng et al.
5,459,056 A  10/1995   Powell et al.
5,597,896 A   1/1997   Montagnier et al.
5,646,032 A   7/1997   Meulen et al.
5,882,912 A   3/1999   Sandstrom et al.

FOREIGN PATENT DOCUMENTS

DE     43 18387 A1    12/1994
WO     WO 98/35024     8/1998
WO     WO 00/77177    12/2000

OTHER PUBLICATIONS

"Reactivity of primate sera to foamy virus Gag and Bet proteins", Hahn et al., *Journal of General Virology*, (1994), 75, 2635–2644.
"Phylogenetic Analysis of Primate Foamy Viruses by Comparison of pol Sequences", Schweizer and Neumann–Haefelin, *Virology* 207, 577–582, (1995).
"Genomic Organization and Expression of Simian Foamy Virus Type 3 (SFV–3)", Renne et al., *Virology* 186, 597–608, (1992).
"Transduction of Hematopoietic Cells by Foamy Virus Vectors", Hirata et al., *Blood*, vol. 88, No. 9, (Nov. 1), 1996, pp. 3654–3661.
"Foamy Virus Vectors", Russell and Miller, *Journal of Virology*, vol. 70, No. 1, Jan. 1996, pp. 217–222.

(List continued on next page.)

*Primary Examiner*—Hankyel T. Park
(74) *Attorney, Agent, or Firm*—Needle & Rosenberg, P.C.

(57) ABSTRACT

The present invention comprises spumavirus isolated from humans. More specifically, the spumavirus of the present invention was isolated from humans who had exposure to nonhuman primates. Importantly, the spumavirus of the present invention or antibodies to the spumavirus can be used to detect the presence of spumavirus or antibodies in body fluids, for pathogenicity studies of related viruses, and as a vector for gene therapies. The spumavirus of the invention can also be used for treatment of conditions in humans due to the presence of rapidly dividing cells and for recombinant live virus vaccination.

18 Claims, 5 Drawing Sheets

OTHER PUBLICATIONS

Figure 1:
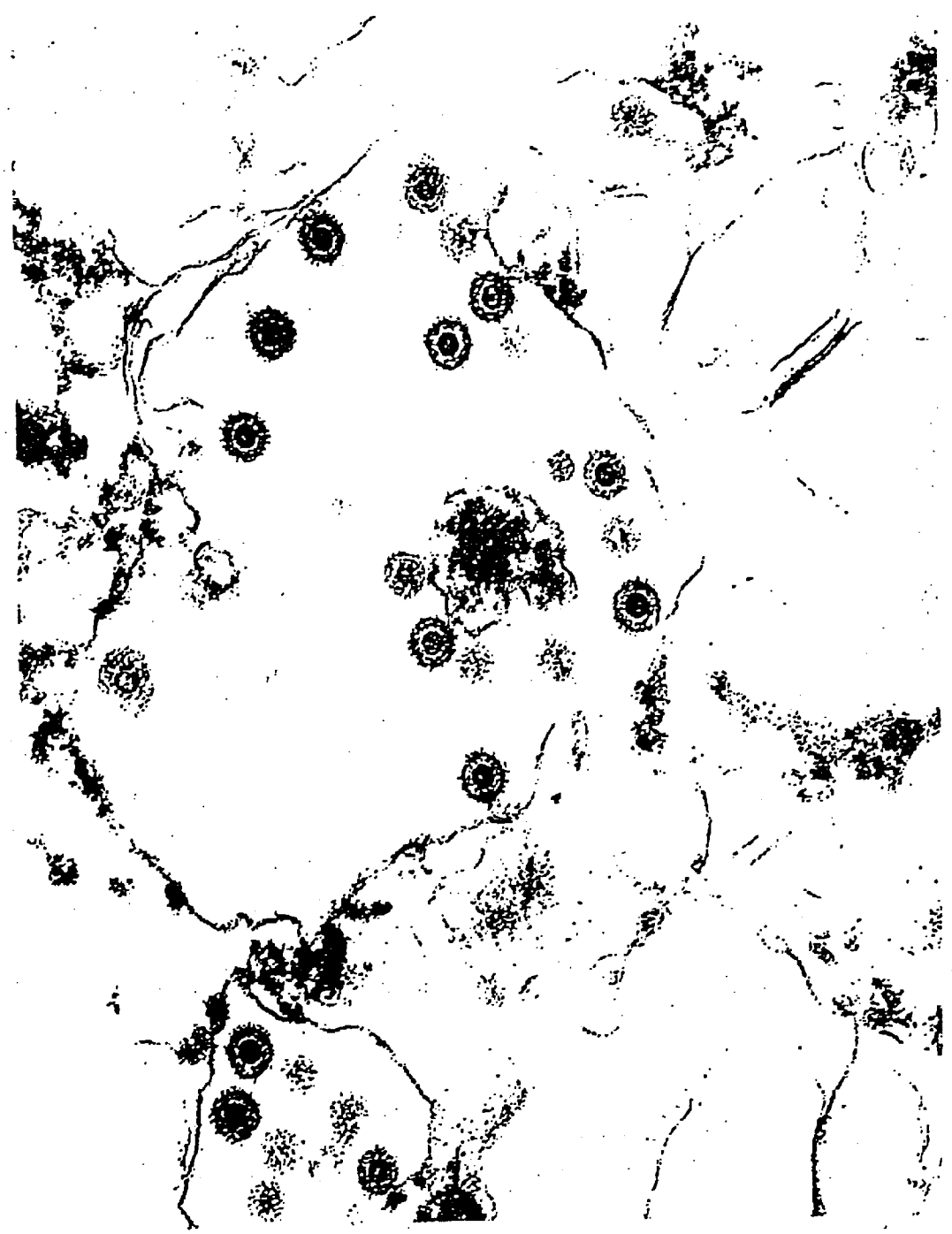

"Detection of Reverse Transcriptase By A Highly Sensitive Assay In Sera From Persons Infected With Human Immunodeficiency Virus Type 1", Walid Heneine, et al., *The Journal of Infectious Diseases*, May 1995, pp. 1210–1216.

"Spumaviruses", Philip C. Loh, *The Retroviridae*. vol. 2, 1993, pp. 361–397.

"Cell tropism of the simian foamy virus type 1 (SFV–1)", Ayalew Mergia et al., *Journal of Medical Primatology*. Jul. 21, 1995, pp. 2–7.

"Isolation of Novel Human Endogenous Retrovirus–Like Elements with Foamy Virus–Related pol Sequence", Agnes Cordonnier et al., *Journal of Virology*, vol. 69, No. 9, Sep. 1995, pp. 5890–5897.

"Identification and Characterization of the Bel 3 Protein of Human Foamy Virus", Jakob Weissenberger and Rolf M. Flugel, *Aids Research and Human Retroviruses*. vol. 10, No. 5, 1994.

"Human Foamy Virus Polypeptides: Identification of env and bel Gene Products", Marie–Louise Giron et al., *Journal of Virology*, vol. 67, No. 6, Jun. 1993, pp. 3596–3600.

"Isolation, Cloning, and Sequencing of Simian Foamy Viruses from Chimpanzees (SFVcpz); High Homology to Human Foamy Virus (HFV)", Ottmar Herchenroder et al., *Virology* 201, 1994, pp. 187–199.

"Isolation of a New Foamy Retrovirus from Orangutans", Myra O. McClure et al., *Journal of Virology*, vol. 68, No. 11, Nov. 1994, pp. 7124–7130.

"Specific enzyme–linked immunosorbent assay for the detection of antibodies to the human spumavirus", Christoph Mahnke et al., *Journal of Virological Methods*, 29, 1990, pp. 13–22.

"The Foamy Viruses," John J. Hooks et al., *Bacteriological Reviews*. Sep. 1975, vol. 39, No. 3, pp. 169–185.

"Simian Foamy Virus Isolated from an Accidentally Infected Human Individual", Matthias Schweizer et al., *Journal of Virology*, Jun. 1997, vol. 71, No. 6, pp. 4821–4824.

"No Evidence of Antibody to Human Foamy Virus in Widespread Human Populations", Munaf Ali et al., *Aids Research and Human Retroviruses*, vol. 12, No. 15, 1996, pp. 1473–1483.

"Markers of Foamy Virus Infections in Monkeys, Apes, and Accidentally Infected Humans: Appropriate Testing Fails to Confirm Suspected Foamy Virus Prevalence in Humans", Matthias Schweizer et al., *Aids Research and Human Retroviruses*, vol. 11, No. 1, 1995, pp. 161–170.

"Persistent Zoonotic Infection of a Human with Simian Foamy Virus in the Absence of an Intact orf–2 Accessory Gene", Margaret E. Callahan et al., *Journal of Virology*, Nov. 1999, vol. 73, No. 11, pp. 9619–9624.

Anonymous Survey for Simian Immunodeficiency Virus (SIV) Seropositivity in SIV—Laboratory Researchers—United States, 1992. *MMWR Morb. Wkly Rep.* 41(43):814–815 (Oct. 30, 1992).

Chapman et al. Xenotransplantation and xenogeneic infections. *N. Engl. J. Med.* 333:1498–1501 (Nov. 30, 1995).

DHHS Docket No. 96M–0311. Draft Public Health Service (PHS) Guideline on Infectious Disease Issues in Xenotransplantation. *Federal Register* 61(185):49919–49932 (Sep. 23, 1996).

EMBL Database; EMVRL: AF049085; Accession No. AF049085 (Aug. 3, 1998).

EMBL Database; EMVRL; AF049084; Accession No. AF049084 (Aug. 3, 1998).

Heneine et al. Absence of evidence for human spumaretrovirus sequences in patients with Graves' disease [letter]. *J. Acq. Immune Defic. Synd. & Human Retrov.* 9(1):99–101 (1995).

Heneine et al. Identification of a human population infected with simian foamy viruses. *Nat. Med.* 4(4):403–407 (Apr. 1998).

Heneine et al. Lack of evidence for infection with known human and animal retroviruses in patients with chronic fatigue syndrome. *Clin. Infec. Dis.* 18(Suppl. 1):S121–125 (1994).

Neumann–Haefelin et al. Nonhuman Primate Spumavirus Infections Among Persons with Occupational Exposure—United States, 1996. *MMWR Morb. Mort. Wkly Rep.* 46(6):129–131 (Feb. 14, 1997).

Neumann–Haefelin et al. Foamy viruses. *Intervirology* 35:196–207 (1993).

Perspectives in Disease Prevention and Health Promotion Guidelines to Prevent Simian Immunodeficiency Virus Infection in Laboratory Workers and Animal Handlers. *MMWR Morb. Mort. Wkly Rep.* 37(45):693–694and 699–704 (Nov. 18, 1988).

Schweizer et al. Phylogenetic Analysis of Primate Foamy Viruses by Comparison of pol Sequences. *Virology* 207:577–582 (1995).

Schweizer et al. Absence of foamy virus DNA in Graves' disease. *AIDS Res. & Human Retrov.* 10(5):601–605 (1994).

Simonsen et al. Absence of evidence for infection with the human spuma retrovirus in an outbreak of Meniere–like vertiginous illness in Wyoming, USA [letter]. *Acta Otolaryngol (Stockh)* 114:223–224 (1994).

Khabbaz et al. Simian immunodeficiency virus needlestick accident in a laboratory worker. *Lancet* 340:271–273 (1992).

Khabbaz et al. Brief report: Infection of a laboratory worker with simian immunodeficiency virus. *N. Eng. J. Med.* 330:172–177 (1994).

SIMIAN FOAMY VIRUS PERCENT NUCLEOTIDE IDENTITY

| | Case1 | Case2 | Case3 | SFV 3 AGM | SFV BAB | SFV MAC | HFV | SFV CPZ | SFV PYG | SFV8 SPM |
|---|---|---|---|---|---|---|---|---|---|---|
| Case1 | - | 82.6 | 82.1 | 87.5 | 82.4 | 77.4 | 68.7 | 66.6 | 67.2 | 66.4 |
| Case2 | - | - | 95.5 | 81.7 | 92.7 | 76.2 | 68.3 | 66.4 | 68.9 | 62.3 |
| Case3 | - | - | - | 82.1 | 93.9 | 76.9 | 67.5 | 66.5 | 69.3 | 62.3 |

FIG. 5

RETROVIRUS ISOLATED FROM HUMANS

CROSS REFERENCE TO RELATED APPLICATIONS

This application is a divisional application of and claims priority to Ser. No. 09/692,652 filed on Oct. 19, 2000, now U.S. Pat. No. 6,492,165, which is a continuation-in-part of and claims priority to U.S. patent application Ser. No. 09/367,213 filed on Dec. 8, 1999, (national phase application of PCT Application No. PCT/US98/02598, filed Feb. 12, 1998) which is abandoned, which is a continuation-in-part of and claims priority to U.S. patent application Ser. No. 08/798,071, filed Feb. 12, 1997, now U.S. Pat. No. 5,882,192, which applications are hereby incorporated herein in their entirety.

This invention was made by the Centers for Disease Control and Prevention, an agency of the United States Government.

TECHNICAL FIELD

The present invention relates to a novel retrovirus, a spumavirus that has been isolated from humans. More particularly, the novel spumavirus may be used as a vector for gene therapy. The novel spumavirus may also be used as a recombinant live virus vaccine.

BACKGROUND OF THE INVENTION

Spumavirus, also known as foamy virus for the characteristics of vacuolization the virus induces in cell culture, belongs to a distinct group of retroviruses. The simian foamy viruses (SFVs) include isolates from Old World and New World monkeys and are classified into 10 different serotypes based on serological cross-reactivities. Virus appears to persist in the host for a long period of time in a latent form and can exist in the presence of neutralizing antibody.

Currently the most studied retrovirus, Human Immunodeficiency Virus, is believed to be derived from nonhuman primate transmission into humans at some past time. Concerns about the risk of transmission of retroviruses from non-human primates to humans working in research laboratories were heightened in the early 1990's when two persons developed antibodies to SIV (Simian Immunodeficiency Virus) following work-related exposures, one of whom had clear evidence of persistent viral infection. (See CDC. Anonymous survey for simian immunodeficiency virus (SIV) seropositivity in SIV laboratory researchers—United States, 1992. MMWR Morb Mort Wkly Rep 1992; 41: 814–5; Khabbaz R. F., et al. Brief report: infection of a laboratory worker with simian immunodeficiency virus. New Eng J Med. 1994; 330: 172–7; Khabbaz R F, et al. Simian immunodeficiency virus needlestick accident in a laboratory worker. Lancet 1992; 340: 271–3; and CDC. Guideline to prevent simian immunodeficiency virus infection in laboratory workers and animal handlers. MMWR 1988; 37:693–704.) In addition to SIV, nonhuman primate species used in biomedical research are commonly infected with SFV (simian foamy virus), STLV (simian t-cell lymphotrophic virus), and/or type D retroviruses. All of these retroviruses cause lifelong infections in nonhuman primates, and some are known to be transmissible through sexual contact, blood, or breast-feeding. Natural SFV infections in non-human primates have not been definitively associated with disease. In non-human primates, infection with the other retroviruses may result in a clinical spectrum ranging from asymptomatic infection to life threatening immunodeficiency syndromes or lymphoproliferative disorders. The transmission routes of SFVs among nonhuman primates remain undefined, but the prevalence of seroreactivity is high among captive adult non-human primates.

Studies of the prevalence of spumavirus infection of humans are limited and the findings are not definitive. Though there is some evidence of human infection with SFV (antibodies and positive PCR results), such occurrence has been reported in only two persons, both of whom had occupational risks for infection. Associated disease was not reported in either. (See Schweizer M., et al. Absence of foamy virus DNA in Graves' disease. AIDS Res & Human Retrov 1994; 10: 601–5; Neumann-Haefelin D, et al., Foamy viruses. Intervirology 1993; 35: 196–207; and Schweizer M, et al., Markers of foamy virus infections in monkeys, apes, and accidentally infected humans: appropriate testing fails to confirm suspected foamy virus prevalence in humans. AIDS Res & Human Retrov 1995; 11: 161–70.) There have been no published reports that virus was ever isolated from these infected individuals.

Other inconclusive evidence was seen in early studies which described a relatively high rate of seroreactivity to antibodies to spumaviruses among human populations not known to be exposed to non-human primates. In some instances seroreactivity was suggestively linked to human disease, including disorders of the central nervous system, thyroid disease, and Chronic Fatigue Syndrome. In most instances these studies lacked definitive evidence of human infection and were not subsequently confirmed. (See Heneine W, et al., Absence of evidence for human spumaretrovirus sequences in patients with Graves' disease [letter]. J Acq Immune Defic Synd & Human Retrov. 1995; 9: 99–101; Simonsen L, et al.,. Absence of evidence for infection with the human spumaretrovirus in an outbreak of Meniere-like vertiginous illness in Wyoming, USA [letter]. Acta Oto-Laryngologica 1994; 114: 223–4; and Heneine W., et al., Lack of evidence for infection with known human and animal retroviruses in patients with chronic fatigue syndrome. Clin Infect Dis 1994; 18: S121-5).

To the knowledge of the inventors, there has not been a documented, definitive isolation of a spumavirus, such as the one of the present invention, from humans. Previous reports of human spumavirus isolates are now widely regarded as laboratory contaminants.

Recent publications indicate that earlier serological tests showing human spumavirus antibodies in the human population were incorrect. Immunological investigation of a previously reported human spumavirus revealed that it shared common antigens in complement fixation, immunofluorescence and neutralization assays with the chimpanzee foamy virus, SFV-6. Furthermore, failure to detect serological evidence of HFV infection in people from a wide geographical area suggested that this virus isolate was a variant of SFV-6, particularly since sera from chimpanzees naturally infected with SFV-6 neutralized both viruses. In a survey for prevalence of human foamy virus in more than 5000 human sera, collected from geographically diverse populations, none of the serum samples were confirmed as positive. Taken together with sequence analysis endorsing the phylogenetic closeness of the purported human spumavirus to SFV-6/7, these data strongly suggest that human foamy virus is not naturally found in the human population. (See Ali, M. et al., "No Evidence of Antibody to Human Foamy Virus in Widespread Human Populations," AIDS Research and Human Retroviruses, Vol. 12, No. 15, 1996.)

Recent concern that xenotransplantation, the use of living tissues from nonhuman species in humans for medical purposes, may introduce new infections into the human community has increased the importance of defining the ability of simian retroviruses to infect and/or cause disease in humans (See Chapman L E, et al. Xenotransplantation and xenogeneic infections. New Engl J Med 1995; 333: 1498–1501; DHHS. Docket No. 96M-0311. Draft Public Health Service (PHS) Guideline on Infectious Disease Issues in Xenotransplantation. Federal Register Vol. 61, No. 185. Sep. 23, 1996.). The primary animal species considered as donors for xenografts are baboons and pigs. Thus, what is needed are compositions and methods for detecting viruses that may be transmitted from the nonhuman organ donors to the recipient human. Additionally, information regarding these transmissible agents may provide valuable information about the organ donors' cellular receptors that may be important for transplantation success.

Gene therapies have long looked for a good vector that can transport the foreign gene of choice into human cells. The lack of any known disease associated with the virus of the present invention makes the present invention an ideal candidate for gene therapy regimens. Thus, compositions and methods for gene therapy are needed that use a vector capable of carrying a significant amount of foreign DNA that will enter the host organism and not cause disease.

Compositions and methods for vaccination using recombinant live retroviruses are also needed. A live virus, that causes no illness in humans, and that has genes of antigens of choice incorporated into its genome, would provide for an excellent vaccination tool. The retrovirus would reproduce in the human host and expose the immune system to antigens so that an immune response can be initiated.

Targeted attack on reproducing cells is a goal of cancer treatment. What is needed is are compositions and methods for cancer treatment that are specific for dividing cells that do not cause systemic damage to the cancer patient. A virus that could infect and kill dividing cells, without killing other cells of the host would provide a solution for cancer treatment.

SUMMARY OF THE INVENTION

The present invention is directed to compositions and methods comprising a novel spumavirus or foamy virus, known as SFVHu-1. The present invention comprises a spumavirus isolate of human origin that has been definitively isolated from a human with no disease. The novel spumavirus of the present invention has been maintained through tissue culture cells where it causes the characteristic vacuolation of the cells that is known for foamy viruses.

The novel spumavirus of the present invention has utility as a reagent for the immunological screening of the human population for the prevalence of such viruses in the population. The novel spumavirus of the present invention can also serve as a vector in gene therapy because the virus appears to cause no disease in humans and is not transmitted to other humans. Additionally, the novel spumavirus of the present invention can be used as a reagent in pathogenicity studies of these and related viruses. Moreover, the sequences of the novel spumavirus of the present invention can be used as probes to detect virus in biological samples. Vectors include, but are not limited to, prokaryotic, eucaryotic and viral vectors. The foamy virus of the present invention can also be used as a live recombinant virus vaccine. Additionally, the spumavirus of the present invention can be used as a replicating viral system to kill live dividing cells, either in vitro or in vivo.

The spumaviruses or foamy viruses are by far the least well characterized of the retroviruses. They have been isolated as agents that cause vacuolation ("foaming") of cells in culture from a number of mammalian species, including monkeys, cattle, cats, and reportedly in humans. Persistent infection with these viruses is not associated with any known disease.

Recent studies using improved diagnostic assays have shown no evidence of foamy virus infection of humans in studies of large populations (approximately 8,000 persons). Given these results, the identification of seroreactivity in three persons occupationally exposed to non-human primates is notable. The PCR identification of viral genome sequences in biologic specimens from all three, and isolation of the virus from one, confirm virus infection in these workers.

The present invention includes the isolation and characterization of a spumavirus, SVFHu-1, that was shown to have been transmitted from non-human primates to humans at some point in the past. The spumavirus of the present invention does not appear to be readily transmitted from human to human. The spumavirus of the present invention can be used in constructing protocols for diagnosing spumavirus infections and may be used as a vector in gene therapy procedures.

The present invention also includes methods and compositions for detecting spumavirus in biological fluids. The methods and compositions, including kits, can be in any configuration well known to those of ordinary skill in the art. The present invention also includes antibodies specific for the spumavirus and antibodies that inhibit the binding of antibodies specific for the spumavirus. These antibodies can be polyclonal antibodies or monoclonal antibodies, which also includes fragments of any type of antibody. The antibodies specific for the spumavirus can be used in diagnostic kits to detect the presence and quantity of spumavirus in biological fluids or in organs from nonhuman primates for xenotransplantation. Antibodies specific for spumavirus may also be administered to a human or animal to passively immunize the human or animal against spumavirus, thereby reducing infection after accidental exposure to nonhuman primate bodily fluids.

The present invention also includes compositions and methods, including kits, for detecting the presence and quantity of antibodies that bind spumavirus in body fluids. The methods, including kits, can be in any configuration well known to those of ordinary skill in the art. Such kits for detection of spumavirus itself or detection of antibodies to the spumavirus can be used to monitor the blood supply for the presence of spumavirus in the blood supply.

The present invention also includes methods and compositions comprising recombinant live virus vaccines. The virus of the present invention has areas of its genome that make it ideal for the insertion of exogenous genes. The genes can code for any protein for which vaccination or gene therapy is desired. Because SFVHu-1 replicates at a higher level than other known foamy viruses, it is capable of providing a high level of antigen to the host carrying the virus. After administration of SFVHu-1 to the host, the virus would infect the cells, replicate and provide protein antigens to the immune system of the host. A novel aspect of such recombinant live viruses is that SFVHu-1 does not cause disease in the host organism. Additionally, there is no transmission from one host organism to other non-infected host organisms, even by close contact with exchange of bodily fluids. The recombinant live virus vaccines of the present invention are a safe way to provide antigen in a most optimum method to the immune system.

The present invention further includes methods and compositions for the use of replicating viral system to kill live dividing cells in a host or in vitro. In in vitro uses, SFVHu-1 can be used to detect and kill rapidly dividing cells. Foamy viruses, including SFVHu-1, can infect a wide variety of species of cells and can be used in many in vitro cell systems. For example, if the assay of the in vitro cell system required the identification of quiescent cells, application of SFVHu-1 to the tissue culture system would result in the selection of the rapidly dividing cells by SFVHu-1. The tissue culture cells would be infected, but because SFVHu-1 has a productive infection and cytopathic effects only in dividing cells, the dividing cells are killed by such dividing cells would be infected by SFVHu-1 and killed by such infection. The remaining non-dividing cells of the culture would remain alive.

In a host, the ability of SFVHu-1 to infect dividing cells provides an excellent treatment for conditions due to the presence of rapidly dividing cells. For example, a person with disease due to rapidly dividing cells, such as cancer or any known angiogenic condition, could be infected with SFVHu-1. Such virus may or may not carry other, exogenous genes for other effects in the host. Because SFVHu-1 does not cause disease in the host and there is no transmission of the virus to contacts with the host, only the person with the disease from rapidly dividing cells will be treated. In addition, only the rapidly dividing cells of that host person will be infected by SFVHu-1, and the rest of the body will remain uninfected. The virus will infect the rapidly dividing cells and kill them. For example, a person with a fast growing tumor would be infected with SFVHu-1 and the cells of the tumor would be destroyed by the virus. The SFVHu-1 can be recombinantly modified to be selective for cellular receptors on the tumor to make the virus even more specifically targeted to just those cells.

Such treatment with SFVHu-1 could be used for any condition in which rapidly dividing cells provide an aspect of the pathology of the condition. One such condition is the presence of uncontrolled angiogenesis within the body. Angiogenesis dependent diseases are well known in the art and are caused in part by the rapid growth of blood vessels.

Accordingly, it is an object of the present invention to provide a composition comprising a novel spumavirus.

It is another object of the present invention to provide a method of detecting a spumavirus.

It is yet another object of the present invention to provide methods and compositions for detecting the presence and amount of spumavirus in a body fluid or organ.

A further object of the present invention is to provide compositions and methods for treating genetic and physiologic disorders using gene therapy techniques comprising the novel spumavirus of the present invention as a vector for nucleic acid sequences and antisense sequences.

Another object of the present invention is to provide compositions and methods useful for manipulating the expression of genes.

Yet another object of the invention is to provide vaccines.

Yet another object of the present invention is to provide compositions and methods for treating viral infections in humans or animals.

Another object of the present invention is to provide compositions and methods that are effective in treating genetic diseases.

Yet another object of the present invention is to provide a method of treating microbial infections in humans or animals.

It is another object of the present invention to provide for treatments of conditions that are caused in part by rapidly dividing cellular growth.

Another object of the present invention is to provide live recombinant virus vaccines.

An object of the present invention is to provide diagnostic tools such as antibodies or antigens for the monitoring of the blood supply or organ and tissue donation for the presence of spumavirus.

These and other features and advantages of the present invention will become apparent after a review of the following detailed description of the disclosed embodiments and the appended claims.

BRIEF DESCRIPTION OF THE DRAWINGS

FIG. 1 shows a transmission electron microscope photomicrograph of viral particles in Cf2Th canine thymocytes.

FIG. 2 shows tissue culture AMP-reverse transcriptase activity in canine thymocyte cells (Cf2Th) co-cultured with peripheral blood lymphocytes from an infected case worker. Along the baseline is another line showing control Cf2Th cells that were co-cultured with normal human peripheral blood lymphocytes, indicating there was no constitutive reverse transcriptase activity in these cultures.

FIG. 3 is a Western blot of sera from Case A, Case B and Case C and the sera of spouses of two of the cases. The sera was tested against the whole cell lysate from Cf2Th cells infected with the spumavirus isolate. Whole cell lysate of uninfected Cf2Th were used as a control for seroreactivity towards nonviral proteins. In addition, the sera of Case B provide a view of the history of infection because of the existence of Case B sera obtained in 1967, and in 1978, 1980, and 1981.

FIG. 4 is a phylogenetic tree showing the relationships between the sequences of the viruses of the novel spumavirus of the present invention and known spumaviruses.

FIG. 5 is a comparison of the nucleotide homology of the sequenced portion of the present invention and other retroviruses.

DETAILED DESCRIPTION OF THE INVENTION

In response to the identification of simian immunodeficiency virus infection in an occupationally exposed workers, Centers for Disease Control and National Institutes for Health collaborated in an anonymous serosurvey of persons with similar work exposures. Simian immunodeficiency virus seroreactivity was present in 3/427 (0.64%) stored serum samples from these anonymous workers (See CDC. Anonymous survey for simian immunodeficiency virus (SIV) seropositivity in SIV laboratory researchers—United States, 1992. MMWR *Morb Mort Wkly Rep* 1992; 41: 814–5; Khabbaz R F, et al.,. Brief report: infection of a laboratory worker with simian immunodeficiency virus. *New Eng J Med.* 1994; 330: 172–7). Consequently, a voluntary testing and counseling program was developed that allowed linkage between specific exposures or health outcomes and serostatus of persons occupationally exposed to simian immunodeficiency virus. The workers enrolled in this voluntary linked prospective simian immunodeficiency virus surveillance are also at occupational risk for exposure to other retroviruses common in nonhuman primates (nonhuman primates).

Therefore, in 1995, the linked surveillance was expanded to include voluntary testing and counseling for exposure to simian spumaviruses (more commonly called simian foamy viruses, or SFV), simian T-lymphotropic viruses (STLV), and simian type D retroviruses. 1,823 samples from 13 institutions in the United States had been tested for simian immunodeficiency virus; samples from 231 of the participating volunteer workers were also tested for other retroviruses from non-human primates. Three of these 231 workers (1.3%) were determined to be infected with a SFV-like virus by serology and PCR.

An immunofluorescent assay that was developed using cells infected with SFV serotype 3 identified antibodies to a SFV-like virus in recently collected serum specimens from all three workers. The 3 specimens were also western blot positive, showing reactivity to both p70 and p74 gag precursor bands of SFV-3 antigen. Repeat testing of additional sera obtained from these 3 workers at later time points are also positive in both assays. (These workers or cases are herein identified individually as Case A, Case B, and Case C.)

Additional blood samples from these three cases were tested for SFV proviral DNA sequences using polymerase chain reaction (PCR) assays employing primer sets from two regions of the polymerase gene that are conserved among known primate foamy viruses. All three cases were PCR positive in both regions. The PCR products from one region were sequenced. The sequences from each case were distinct from each other but all showed greater than 80% homology to known non-human primate foamy virus sequences. The partial sequences, produced with DNA polymerase PCR primer, of the viral sequence of the present invention is shown below. Seq. ID 1 is a viral DNA sequence isolated from infected Cf2Th cells and Seq. ID 2 is a viral DNA sequence isolated from PBLs from Case A. There is 99.76% homology between the two sequences. The corresponding RNA sequences and resulting proteins can be deduced from these sequences.

```
                                                  Seq. ID 1
TTACTACAAGGACAATATCCAAAAGGTTTTCCAAAACAATATCAATA
TGA

ACTTAATGAAGGACAAGTTATAGTAACTCGTCCTAATGGACAAAGA
ATTA

TTCCTCCAAAATCAGACAGGCCTCAAATTATTTTGCAAGCACATAAT
ATT

GCACATACAGGAAGAGATTCAACCTTTCTTAAGGTCTCTTCCAAGTA
TTG

GTGGCCAAATCTTAGAAAGGATGTGGTTAAAGTTATCAGACAATGTA
AGC

AATGTCTGGTCACAAATGCAGCTACCTTAGCTGCGCCTCCAATACTG
AGG

CCTGAAAGACCTGTAAAGCCTTTTGATAAATTTTTTGTTGACTATATT
GG

CCCTTTACCCCCTTCTAATGGGTACTTACATGTCCTTGTAGTAGTCGA
TG

GTATGACTGGATTTGTATGGTTA

Seq. ID 2
TTACTACAAGGACAATATCCAAAAGGTTTTCCAAAACAATATCAATA
TGA

ACTTAATGAAGGACAAGTTATAGTAACTCGTCCTAATGGACAAAGA
ATTA

TTCCTCCAAAATCAGACAGGCCTCAAATTATTTTGCAAGCACATAAT
ATT

GCACATACAGGAAGAGATTCAACCTTTCTTAAGGTCTCTTCCAAGTA
TTG

GTGGCCAAATCTTAGAAAGGATGTGGTTAAAGTTATCAGACAATGTA
AGC

AATGTCTGGTCACAAATGCAGCTACCTTAGCTGCGCCTCCAATACTG
AGG**

CCTGAAAGACCTGTAAAGCCTTTTGATAAATTTTTTGTTGACTATATT
GG

CCCTTTACCCCCTTCTAATAGGTACTTACATGTCCTTGTAGTAGTCGA
TG

GTATGACTGGATTTGTATGGTTA
```

The relationship between each of the isolates and other known spumaviruses is shown in FIG. 5 which is a phylogenetic tree showing the percent homology of the nucleotide sequences of these viruses and in FIG. 6.

The 5' end of the LTR of SFVHu-1, of 1567 nucleotide bases, has also been sequenced, and is shown as Seq. ID 3.

```
  1  TTCCCAATAA ACATCATCCT GGGTGGACTA GACATCTTAC TAAATTCAAG
 51  ATATCTAGAT TCTCCACTCC TGCTGATGTC CAGAAAATTG TGGATGAGCT
101  TCTCCCTAGA GGAGCAAGCA TTGTAATGCC TGATGGAACA AAGTATCCAA
151  GTACCAGAAA AGTGCACTTA GTCAATGAAG GAACCCTTGT AGAATACCAA
201  GCCAAATGTA AGGAGATAGA GGAAAAGTAC GGAGGATGCT TTTCTACAGA
251  TAGTGATGAT GACAGTGATG ATTACTCTGA GGATACTCCA GAAACTGAAA
301  CCACTGATGT GGAATAGAGT ACAGTGTTAA GGATTCACAT AATCTGCCTA
351  GCAACTGCTT ATGCTTAAGA ATGAATCAGT ATATTGTTTA GGAATAAGTT
401  ATAGTTTATA AGAAGTTAAT CCTTAGGGAG TATTTGGTGG AAATGACTGA
451  GTGACATGAA GTTTATTCAC CATACTCTCA ATAGGAGCCA CTAGTTGAGC
```

-continued

```
 501 CTGTGCGTTC AAATCCATGC TCAGCTTAAG TGACTCCCTT TTAGTTTCAC
 551 TTTAAGTTAA GTTAGGAATA AGTTCCATAT AATCCTAAGG GAGTATGTGG
 601 ACCTTCTTGT TAGGAAATAG TTTAAGATAG TCCACAGCTC CCTTCTTTTT
 651 GAGTTCTAGT CTTTGTTAAG TTTGTTGGCT CATACAGATA AAGTGCTCAT
 701 TAAACAGGAA ACCGCAACCG GGTAAAGGTT AGCACAGTAA ATTAAGCTAG
 751 CAGTTACTCA AGAGCCCGGT AAGCATTCAA GTAGTTCGAA TCCCTTTAAT
 801 GCTGACGGAT TGCTCTTTAG TGAGGTGATG TAATCTGTTT TTGCAATCTG
 851 AAATGTGTGT TTGCACAGGA AGTTGTACAA GAAAGGGAAT GGCTAAACTT
 901 GTTACAGTTC GAACAAACAT TTAGCAATTT CCTTTGCTTT TGGAGTTCGA
 951 GCCTTGTACT TATACTTTGA GCATATGTAT TGTAACACCT AAGTATGGAA
1001 AAATCTCCAA GTATGAGTCA CGAGATGCTT GGCTCACTGC GTTGGACGAC
1051 TGGAAAGAAG CTTCAACAGT CGGACAGCA TCTCGAAGAA GGCCTCCGGA
1101 ATGAAAGAGT GAAAAATGAA GTCTCCTCAT TCAGAGAGCC TTCTTTTAGA
1151 ATTTCAGGCA GAATAGAGTT TCCAATAGAA TAAACTTTTG TATTAGCAGA
1201 TAGATAGGAT ATATAATCTC TGCTTTAGAT TGTACGGGAG CTCACCACTA
1251 CTCGCTGCGT CGAGAGTGTT CGAGTCTCTC CAGGCTTGGT AAGATATAAA
1301 CTTTGGTATT CTCTGTATTC TTATGATCCA ATATTACTCT GCTTATAGAT
1351 TGTAATGGGC AATGGCAATG CTTTATCAAT GAATGATTTT ATGGTGAATT
1401 AAGTTCATAT ATGTTTTAAG AAGTTTAACA ATAAACCGAC TTAATTCGAG
1451 AACCAGATTT ATTAGTATTG TCTCTTTCTA TACTTTAAGT AAAGTGAAAG
1501 GAGTTGTATA TTAGCCTTGC TTATAAGAGC CATCTAGTGG TATAAGTGTG
1551 TACTACACTT ATCTAAA
```

A 3' internal region of SFVHu-1 has also been sequenced. This sequence includes ORF 1 (Open Reading Frame) and ORF-2, which are overlapping genes, and includes 3' sequence from env and bel genes. This sequence is identified as Seq. ID 4 and contains 2406 nucleotides. This sequence is analogous to SFV-3 bases 8953 to 11,356.

```
  1 AAGGGGATGT TGAGCAATCC AACATGTGCA TACCCACTTG AATCATCTTA Seq. ID 4

51 AAACCATGTT ACTAATGAGG AAGATTGACT GGACTTTTAT TAAGAGTGAT

101 TGGATTAAAG AACAACTTCA GAAAACTGAA GATGAAATGA AGATTATTAG

151 AAGAACAGCT AAAAGTTTAG TATATTATGT GACTCAAACA TCATCTTCCA

201 CTACAGCAAC ATCATGGGAA ATTGGAATTT ATTATGAAAT AACTATACCA

251 AAACATATTT ATTTGAATAA TTGGCAAGTT GTTAACATAG GTCATCTGAT

301 TGAGTCAGCT GGTCATTTGA CCTTAATAAG GGTTAAACAT CCTTATGAAG

351 ACTTTAATAA AGAATGCACA TATGAACAAT ATTTACATCT TGAAGACTGC

401 ATATCTCAGG ATTATGTGAT TTGTGACACG GTACAAATAT TGTCACCATG

451 TGGAAACTCA ACAGTAACCA GTGACTGCCC TGTCACTGCT GAAAAGGTAA

501 AGGAACCATA TATTCAAGTG TCAGCTTTAA AAAATGGAAG CTATTTGGTT

551 CTAACCAGTA GAACAGATTG CTCAATACCA GCATATGTTC CCAGCATTGT

601 AACTGTGAAC GAAACAGTTA AGTGTTTTGG GGTTGAGTTT CATAAACCAC

651 TATACTCAGA AAGTAAAGTC AGCTTTGAAC CACAAGTTCC ACATCTGAAA
```

```
                     -continued
 701 CTACGCTTGC CACATCTGGT TGGGATTATT GCAAGTCTTC AAAATTTGGA

751 AATTGAAGTA ACNAGCACCC AAGAGAGTAT ANAAGATCAG ATTGAAAGAG

801 TTCAATCACA GCTTCTTCGG CTGGACATTC ACGAGGGAGA CTTTCCTGCT

851 TGGATTCAAC AACTTGCTTC TGCAACCAAG GACGTCTGGC CTGCAGCTGC

901 TAAAGCTCTT CAAGGCATAG GTAACTTTTT ATCTAATACT GCCCAGGGAA

951 TATTTGGAAC TGCTGTAAGT ATTCTATCCT ATGCCAAGCC TATTCTTATA

1001 GGAATAGGTG TTATACTTTT GATTGCATTC TTGTTTAAGA TTGTATCATG

1051 GCTTCCTGGG AAGAAGAAAA AGAACTAGGA CATCTGCATC TTCCAGAAGA

1101 CGATCCTCTG CCCAATTTAG ATGTGCTCCT GGGTCTTGAT CATATGGAAT

1151 CCAATGAAGG ACCTGATCAA AATCCAGGAG CTGAAAAGAT CTACATTCAA

1201 CTCCAAGCAG TCCCAGGGGA AGCCTCAGAG AAAACTTACA AATTTGGATA

1251 TGAAGACAAA GAGGCACAAA ATCCTGACTT AAAAATGAGA AATTGGGTTC

1301 CTAACCCCGA CAAAATGAGT AAGTGGGCCT GTGCAAGGCT TATTCTTTGT

1351 GGACTTTATA ATGCAAXAAA GGCTGGAGAA CTCTTGGCTA TGGACTATAA

1401 TGTTCAATGG GAACAATCAA AAGAAGACCC AGGATACTTT GAAGTGGAAT

1451 ATCACTGTAA AATGTGCATG ACTGTTATTC ATGAACCTAT GCCTATCCAA

1501 TATGATGAAA ANACTGGATT ATGGCTAAAA ATGGGTCCCC TTAGGGGAGA

1551 TATAGGATCT GTAGTACATA CTTGTAGAAG GCATTACATG AGATGTTTGT

1601 CTGCCCTTCC TAGCAATGGA GAACCTCTCA AACCTAGAGT CCGGGCTAAT

1651 CCTGTCCGAA GATATCGAGA GAAGCAAGAG TTCGTTGCGA CTAGGCCTAA

1701 ACGCTCCAGA TGGGGTGTGG CCCCTAGCGC AGACTCCCAT ACTTCCAGTG

1751 GTGACGCCAT GGCCCTTATG CCAGGACCAT GCGGCCCCTT CGGTATGGAC

1801 ACTCCTGGTT GCTTACTGGA AGGGATACAA GGATCAGGGC CTGGAACCTC

1851 CGAAATGGCT GTGGCAATGT CAGGAGGACC TTTCTGGGAA GAAGTGTACC

1901 GGGACTCAAT TCCTGGTGCC CCCACTGGGT CTAGTGAAAA TTAGGCTTTA

1951 TCAAAATCTA ACTGTTGTAA ATGTTTGTGG ATCTGTTGAC CCATGGGAAA

2001 ATGAGAATCC CACTAGAGGT CGCAGAGGGC CTATGCATAG ATATGATTGT

2051 AGAATTGCTT GTGATCCAAG CTATTGCTTT AAGGCTATTT GGGAAGGAAA

2101 CTTTTGGGAC AAAAAAAAAA GGATCAGGCA TGCTGGCTAG TTCATCTGAA

2151 AGAAGGACAT AAATTTGGTG CAGATGAGTT ATCTTCTGGG GATCTTAAAA

2201 TATTAGCAGA ATCTAGACCT TATCCATATG GATCTATTGG TCATTGTGCT

2251 ATGCTTCAAT ATGCAGTACA AGTTAAAATG AGAGTTGATA GAGCTCCTTT

2301 GACCTCAAAG GTGAGAGCTA TTAAAGCTTT GCACTATCAT CGCTGGAATA

2351 TTTGTCAGCT GGAAAATCCT GGCATAGGAG AAGGATTCAG TCCCTCTGGT

2401 AATACACA
```

The entire sequence of SFVHu-1 has been sequenced. The entire sequence is Seq. ID 5.

```
   1 TGTGGCTGAC AGCTACTAAA ATGATTGGCA C

-continued

```
 101 TCCTGGGTGG ACTAGACATC TTACTAAATT CAAGATATCT AGATTCTCCA
 151 CTCCTGCTGA TGTCCAGAAA ATTGTGGATG AGCTTCTCCC TAGAGGAGCA
 201 AGCATTGTAA TGCCAGATGG AACAAAGTAT CCAAGTACCA GAAAAGTGCA
 251 CTTAGTCAAT GAAGGAACCC TTGTAGAATA CCAAGCCAAA TGTAAGGAGA
 301 TAGAGGAAAA GTACGGAGGA TGCTTTTCTA CAGATAGTGA TGATGACAGT
 351 GATGATTACT CTGAGGATAC TCCAGAAACT GAAACCACTG ATGTGGAATA
 401 GAGTACAGTG TTAAGGATTT ACATAATCTG CCTAGCAACT GCTTATGCTT
 451 AAGAATGAAT CAGTATATTG TTTAGGAATA AGCCTTAGTT TATAAGTAGT
 501 TAATCCTTAG GGAGTATTTG GTGGAAATGA CTGAGTGACA TGAAGTTTAT
 551 TCACCATACT CTCAATAGGA GCCACTAGTT GAGCCTGTGC GTTCAAATCC
 601 ATGCTCAGCT TAAGTGACTC CCTTTTAGTT TCACTTTAAG TTAAGTTAGG
 651 AATAAGTTCC ATATAATCCT AAGGGAGTAT GTGGACCTTC TTGTTAGGAA
 701 ATAGTTTAAG ATAGTCCACA GCTCCCTTCT TTTTGAGTTC TAGTCTTTGT
 751 TAAGTTTGTT GGCTCATACA GATAAAGTGC TCATTAAACA GGAAACCGCA
 801 ACCGGGTAAA GGTTAGCACA GTAAATTAAG CTAGCAGTTA CTCAAGAGCC
 851 CGGTAAGCAT TCAAGTAGTT CGAATCCCTT TAATGCTGAC GGATTGCTCT
 901 TTAGTGAGGT GATGTAATCT GTTTTTGCAA TCTGAAATGT GTGTTTGCAC
 951 AGGAAGTTGT ACAAGAAAGG GAATGGCTAA ACTTGTTACA GTTCGAACAA
1001 ACATTTAGCA ATTTCCTTTG CTTTTGGAGT TCGAGCCTTG TACTTATACT
1051 TTGAGCATAT GTATTGTAAC ACCTAAGTAT GGAAAAATCT CCAAGTATGA
1101 GTCACGAGAT GCTTGGCTCA CTGCGTTGGA CGACTGGAAA GAAGCTTCAA
1151 CAGTCGGGACAGCATCTCGA AGAAGGCCTC CGGAATGAAA GAGTGAAAAA
1201 TGAAGTCTCC TCATTCAGAG AGCCTTCTTT TAGAATTTCA GGCAGAATAG
1251 AGTTTCCAAT AGAATAAACT TTTGTATTAG CAGATAGATA GGATATATAA
1301 TCTCTGCTTT AGATTGTACG GGAGCTCACC ACTACTCGCT GCGTCGAGAG
1351 TGTTCGAGTC TCTCCAGGCT TGGTAAGATA TAAACTTTGG TATTCTCTGT
1401 ATTCTTATGA TCCAATATTA CTCTGCTTAT AGATTGTAAT GGGCAATGGC
1451 AATGCTTTAT CAATGAATGA TTTTATGGTG AATTAAGTTC ATATATGTTT
1501 TAAGAAGTTT AACAATAAAC CGACTTAATT CGAGAACCAG ATTTATTAGT
1551 ATTGTCTCTT TCTATACTTT AAGTAAAGTG AAAGGAGTTG TATATTAGCC
1601 TTGCTTATAA GAGCCATCTA GTGGTATAAG TGTGTACTTA CACTTATCTA
1651 AAGAGGTGGA ATTCTTTAAG GATAACCAAT ATACAAAATT CCACGACAAT
1701 TGGCGCCCAA CGTGGGGCTC GAATATAAGT CGGGTTTTAT TATAAAGACT
1751 TGTTTAAGTC TTAGAATTAT CCCTAGGGAC CTTCACGCAC TGCGGAAGGT
1801 ATAAGTACTC AAAGATGGGT GATCATAATT TGAATGTTCA AGAACTCTTG
1851 AACCTTTTTC AGAATCTAGG TATTTCCAGA CAACCAAATC ATAGAGAAGT
1901 CRTAGGACTT CGTATGACAG GAGGCTGGTG GGGTCCAGGG ACCCGCTATA
1951 ATCTAGTTTC AATCTTTTTA CAAGATGATT CTGGACAACC TTTACAACAA
2001 CCCAGGTGGA GACCTGAAGG TAGACCAGTT AATCCTTTGG TTCATAATAC
2051 TATAGAAGCC CCTTGGGGAG ACTTAAGGTT AGCTTTTGAA GACTTGGATG
```

-continued

```
2101 TAGCAGAAGG TACTTTGAGG TTTGGTCCTT TAGCTAATGG AAATTGGATT
2151 CCTGGAGATG AATACTCCAT GGAATTCCAG CCTCCACTAG CACAAGAAAT
2201 AGCTCAATTA CAAAGAGACG AAATGGAAGA ATATATTGGAT ATAACAGGAC
2251 AAATATGTGC ACAAGTTATA GATTTAGTAG ATATGCAAGA TGCTCAAATT
2301 AGAGGCCYTG AAAGACGTTT ACAAGATAGA CCAGGTTTAA GGGATAACTT
2351 ACCAGTTGCT GGTATACAAG CACCACCATC TAGTCCAATT GGGCAGCCTA
2401 TTGCATCATC TTCACTTCAA CCTGTTCCTG GATCCAGCCA ATCCTCTGCT
2451 GATCTTGGTT GGGAATCAGG AGCGCCTGGG CAAATAGATC CTAGATTGTC
2501 CAGGGTGGCC TATAACCCAT TTTTACCAGG ACCAAGTGAT GGGTCTGGGG
2551 GATCAATCCC AGTCCAGCCT AGTGCTCCTC CAGCGGTTCT TCCATCCTTA
2601 CCCTCACTTC CTGCACCTGT TGCTCAACCT GTTGTTCAGT ATGTTGTTCC
2651 ACCTGCCCCT GCTCCACAAG CTATTCCAAT TCAACACATT CGAGCAGTGA
2701 CAGGAAATAC ACCTACTAAT CCAAGAGATA TTCCTATGTG GCTTGGAAGA
2751 CATTCAGCTG CTATAGAAGG AGTATTTCCT ATGACTACGC CTGATCTTCG
2801 CTGTCGAGTT GTTAATGCTC TTATAGGAGG AAGTCTTGGA CTTTCTTTGG
2851 AGCCTATACA TTGTGTAAAT TGGGCTGCTG TTGTAGCTGC TCTATATGTG
2901 AGAACACATG GATCATATCC CATACATGAA CTAGCTAATG TACTCCGAGC
2951 AGTTGTTAAT CAAGAGGGAG TAGCAACAGG TTTTCAACTT GGAATTATGC
3001 TGTCCAATCA AGATTTTAAT CTTGTTTGGG GAATTCTACG TCCCCTATTG
3051 CCTGGACAAG CTGTAGTCAC AGCTATGCAG CAAARACTTG ATCAAGAAGT
3101 CAGTGACGCT GCTAGGATTG CCTCCTTTAA TGGACATTTA AATGATATAT
3151 ATCAACTTCT AGGACTGAAT GCCCGAGGTC AAAGCATTAC TAGAACTCAG
3201 GGTAGTTCAA TCTCTGGAAC CTCTACTTCT ACAGGCAGAG GAAGGAGAGG
3251 ACAAAGAAAC CAGCAACAGT CTGGTCAACA GCAACAACAA CAGGCAAGAA
3301 GAAGTAATCA GGGAAACCAG AGACAGAGAA ATAATAATCA GAGACAATCC
3351 TCTGGTAATA ATCAGGGACA AGGAGGCCAA GGAGGATATA ATTTGAGACC
3401 CAGAACTTAT CAGCCGCAGC GCTACGGAGG AGGACGTGGA AGAAGATGGA
3451 ACGATAATCA ACAACAGCAA CAAGCACAGC CAGGCAGATC AGCTGATCAA
3501 CCTCGTTCCC AGAGTCAGCA ACCACAAACA GAGGCTCGTG GCGATCAGTC
3551 ACGAACATCT GGTGCTGGGC GCGGACAACA AGGARGAGGG AACCAAAACC
3601 GAAATCAACG CCGGGCTGAT GCTAACAATA CTCGGAATGT GGATACTGTG
3651 ACAGTAACCA CAACTTCCTC CTCCACAACT GGTTCGGGTC AAAATGGATC
3701 CTCTACAGCT CCTCCAGCCC CTGGAAGCAG AAATCAAGGG GACTAAATTA
3751 AAGGCTCATT GGGACAGTGG AGCTACAGTA ACATGTGTTC CACAAGCCTT
3801 TCTAGAAGAT GAAGTACCAA TTAAAAATAT TTGGATCAAG ACAATTCATG
3851 GTGAAAAAGA ACAGCCTGTC TATTATTTAA CCTTTAAAAT MCAAGGAAGA
3901 AAAGTAGAAG CAGAAGTAAT CTCTTCCCCT TATGACTACA TATTAGTCAG
3951 TCCATCTGAC ATCCCCTGGC TAATGAAGAA ACCTCTCCAA TTGACAACTT
4001 TAGTTCCTCT TCAAGAATAC AAAGAAAGAC TTTTAAAGCA AACTATTTTA
4051 ACTGAAAAAT ATAAAGATAG ATTACAATCT TTATTTTTGA AATATGATGC
```

-continued

```
4101 ATTATGGCAA CATTGGGAAA ATCAAGTGGG CCATAGGCGT ATTAAGCCTC
4151 ATCATATAGC AACTGGTACA GTTAACCCTA GACCACAAAA GCAATATCCA
4201 ATTAATCCAA AAGCAAAGCC AAGTATACAA GTTGTAATTA ATGATTTATT
4251 AAAACAAGGT GTGCTAATAC AGCAAAATAG TGTGATGAAT ACTCCTGTAT
4301 ATCCTGTACC AAAACCAGAT GGAAAATGGA GAATGGTTTT AGATTATAGA
4351 GAAGTCAATA AGACCATCCC TTTAATTGCA GCTCAAAATC AACATTCTGC
4401 AGGGATTCTA TCATCCATAT TTAGAGGCAA ATATAAAACC ACTTTAGATT
4451 TATCTAATGG TTTTTGGGCT CATTCTATTA CACCAGAATC TTATTGGTTA
4501 ACTGCTTTTA CTTGGCTTGG ACAACAATAT TGTTGGACAA GATTACCTCA
4551 AGGATTTCTC AATAGTCCTG CTTTATTTAC AGCAGATGTT GTTGATTTAT
4601 TAAAAGAAGT ACCAAATGTA CAAGTTTATG TGGATGATAT TTATATTAGT
4651 CATGATGACC CTGAAGAACA TTTGGACCAA CTTGAGAAAG TGTTTTCGCT
4701 ATTGCTCAAA TGCGGTTATG GGTTTCTCT TAAAAAATCT GAAATTGCTC
4751 AACATGAAGT TGAATTCCTT GGGTTTAATA TTACAAAAGA AGGTCGAGGC
4801 CTAACAGAAA CTTTTAAACA AAAACTCTTA AATATAACTC CACCAAAAGA
4851 TCTGAAACAG TTACAAAGTA TTTTAGGCCT TCTAAATTTT GCAAGGAACT
4901 TTGTTCCTAA TTTTTCTGAA TTAGTTAAAC CCTTATATAA TATCATTGCT
4951 AATGCCAATG AGAAATATAT TACATGGACT TCTGACAATA GTCAACAGCT
5001 ACAATATATA ATTTCATTAT TAAATTCTGC AGAAAACTTA GAAGAAAGAA
5051 ATCCAGAAGT CAGATTAATA ATGAAAGTAA ATACCTCTCC TTCAGCAGGA
5101 TATATACGGT TTTATAATGA ATTTGCTANA AGACCTATTA TGTACTTGAA
5151 TTATGTTTAT ACTAAGGCAG AAGTTAAGTT CACTAACACT GAAAAATTGC
5201 TAACTACTAT ACATAAAGGG TTAATTAGAG CCTTAGATCT TGCCATGGGA
5251 CAAGAAATCT TAGTATATAG TCCTATCGTA TCCATGACCA AAATTCAAAA
5301 AACACCATTA CCAGAAAGAA AAGCTCTACC AATTAGATGG ATAACCTGGA
5351 TGTCTTATTT AGAAGATCCC AGAATACAAT TTCATTATGA TAAGACATTA
5401 CCCGAGCTAC AACAGGTTCC TACTGTCACT GATGATGTTA TAGCTAAGAC
5451 TAAACATCCT AGTGAATTTA ATATGGTCTT CTACACTGAT GGTTCTGCAA
5501 TCAGACATCC AAATGTTAAT AAGTCACATA GTGCTGGAAT GGGTATTGCT
5551 CAAGTACAGT TTAAACCTGA GTTTACAGTT GTTAATACTT GGTCTATTCC
5601 TCTTGGAGAT CATACGGCAC AACTTGCCGA AGTTGCAGCT GTAGAATTTG
5651 CATGTAAAAA GGCCCTCAAA ATAGATGGAC CTGTTTTAAT AGTAACTGAT
5701 AGTTTCTATG TTGCTGAGAG TGCTAATAAG GAATTACCYT ATTGGCAATC
5751 AAATGGGTTC TTTAATAACA AAAAGAAACC CCTTAAACAT GTCTCCAAGT
5801 GGAAGTCAAT TGCAGAATGT GTACAATTAA AGCCTGACAT TACTATTATT
5851 CATGAAAAAG GTCACCAGCC TACTGCTTCA ACATTTCATA CAGAAGGTAA
5901 TAATTTAGCT GATAAGCTTG CCACCCAAGG AAGTTATGTG GTAAATACAA
5951 ATACCACTCC AAGCCTGGAT GCAGAGTTGG ATCAATTACT ACAAGGACAA
6001 TATCCAAAAG GTTTTCCAAA ACAATATCAA TATGAACTTA ATGAAGGACA
6051 AGTTATAGTA ACTCGTCCTA ATGGACAAAG AATTATTCCT CCAAAATCAG
```

-continued

```
6101 ACAGGCCTCA AATTATTTTG CAAGCACATA ATATTGCACA TACAGGAAGA
6151 GATTCAACCT TTCTTAAGGT CTCTTCCAAG TATTGGTGGC CAAATCTTAG
6201 AAAGGATGTG GTTAAAGTTA TCAGACAATG TAAGCAATGT CTGGTCACAA
6251 ATGCAGCTAC CTTAGCTGCG CCTCCAATAC TGAGGCCTGA AAGACCTGTA
6301 AAGCCTTTTG ATAAATTTTT TGTTGACTAT ATTGGCCCTT TACCCCCTTC
6351 TAATRGGTAC TTACATGTCC TTGTAGTAGT CGATGGTATG ACTGGATTTG
6401 TATGGTTATA CCCCACTAAG GCTCCTTCAA CTGGCGCAAC TGTTAAAGCT
6451 CTCAATATGC TCACTAGTAT TGCAGTTCCA AAGGTGATAC ACTCTGATCA
6501 GGGTACAGCA TTCACCTCTG CAACTTTTGC TGATTGGGCA AAAGACAAAG
6551 GTATACATTT GGAATTCAGT ACTCCTTACC ATCCCCAAAG TAGTGGCAAG
6601 GTGGAAAGGA AAAATAGTGA TATAAAACGA CTTTTAACTA AACTGCTTGG
6651 TGGGAGACCT GCTAAGTGGN ATGACCTTCT TTCAGTTGTT CAATTGGCAT
6701 TAAATAATTC ATATAGGCCT CTTTCTTCTA AATATACTCC TCATCAACTT
6751 TTGTTTGGTA TAGATTCAAA TACACCATTT GCAAACTCTG ATACACTTGA
6801 TTTATCAAGA GAAGAAGAAC TCTCTCTTTT ACAGGAAATC AGAACTTCTC
6851 TTTGCCATCC ATCCTCCCCT CCTGCCTCCG TTCGTGTCTG GTCTCCTTCT
6901 GTTGGCCAAT TGGTCCAGGA GAGGGTAGCC AGGCCTGCAT CTTTAAGACC
6951 TCGGTGGCAT AAACCTACTC CTGTTCTGGA AGTCATTAAT CCACGAACTG
7001 TTGTCATTTT GGACCATCTT GGCAACAGGA GAACTGTAAG TGTGGATAAT
7051 TTAAAATTAA CARCTTATCA GAAGGATGGC ACCTCCAATG AATCTGCAGC
7101 AATGGCTATT GTGGAAAAAG ATGAATGAAG CACATTCAGC GTTAGAGAAT
7151 ATTTCAACCC TTACTGAAGA ACAGAAGCAA CAAGTGATTA TTGAGATTCA
7201 ACAAGAAGAA GTAATACCTA CTAGGATGGA CAGAGTAAAG TATCTAGCAT
7251 ATGCATGTTG TGCTACCAGT ACACGTGTCA TGTGTTGGTT ATTTTTGATT
7301 TGTGTGTTGC TAATTATTGT ATTTGTATCT TGTTTTGTCA CTGTTGCTAG
7351 GATTCAATGG AATAAGGATA TTACTGTGTT TGGACCAGTC ATTGATTGGA
7401 ATGTTACCCA TCAAGCAACA TATCAACAGC TTAGAGCTTC CAGAATAGCT
7451 AGATCTTTAA GGGTAGAACA TCCTCATATA TCATATATAT CAATAAATAT
7501 GTCTAGTATA CCACAAGGTG TTATATATAC ACCTCACCCT GAACCTATAA
7551 TCCTCAAGGA GAGGGTTTTA GGGATTTCTC AGGTGTTAAT GATAAATTCT
7601 GAAAATATAG CTAATGTGGC CAATTTGTCT CAAGCACAA AAGTATTGTT
7651 GACTGATATG ATAAATGAGG AATTACAAGA TTTGTCAAAC CAAATGATTG
7701 ACTTCGAATT ACCTCTAGGA GATCCTAGAG ACCAAAATCA ATATGTACAT
7751 CATAAGTGTT ACCAGGAGTT TGCTCATTGT TATTTAGTCA AATATAAAAC
7801 ACNTAAAGAA TGGCCCTCTT CAGCTCTGAT TGCTGATCAG TGTCCCCTAC
7851 CAGGAGAACA TCCAACTGTA CAGTATTCAC ATCAAAATAT ATGGGACTAT
7901 TATGTTCCTT TTCAACAAAT ACGGCCAGAG AAATGGACTT CATCCTTAGT
7951 ATATGAAGAT GCTAGAATAG GGAGCTTCTA TATACCAAAA AATATGAGAA
8001 ACAAGAATGT TACACATGTA ATATTTTGTT CAGATCAATT ATATGGAAAA
8051 TGGTATAATT TGATGAATAC TGTACAAGAA AATGAACAAA TTCAAGTCAT
```

-continued

```
8101 AAAATTAAAA AATATTACCA AATCGGGTAC CTCTCAAGTT AAGGATAGAG
8151 GACTTCCGTC CGCTTGGCAT AAGAATGGTA AAAGTACATA TTTTAGGCCT
8201 ATTAATACTT TGGATATTTG TAATAGACCT GAGTTAGTAT TATTACTCAA
8251 TAGTACTTAT TATACTCTCT CTCTGTGGGA AGGAGATTGT GGATATACTA
8301 GGGAAAATGC TACTCAAGCT AATCCTCTTT GTAAAAACTT TTATAATGAA
8351 TCTAAAAAAC ATTGGCACCC ATACGCATGT AGGTTTTGGA GATATAAAAA
8401 TGATAAAGAA GAGGTTAAGT GTAGAAATGA GGATAAAAAA CACTGTATTT
8451 ATTATCCCCT TTGGGATACC CCGGAAGCCT TATATGATTT TGGATTTTTG
8501 GCATATCTTA ATGCATTCCC TTCACCACTT TGTATTACAA ATCAAACTGT
8551 TAGGGAGCCA GAGTATGAAG TATATTCCTT ATATATGGAA TGTATGAATT
8601 CTGCGGAAAA ATATGGAATA GATAGTGTTT TGTTTGCTTT AAAAACTTTT
8651 TTAAATTTTA CTGGAACACC AGTGAATGAA ATGCCAACAG CCAGAGCATT
8701 TGTAGGCCTG ACTGATCCTA AATTCCCTCC AGTATATCCA AATATTACTA
8751 AAGAACGAAG AGGATGTGAC AATTCAAGAA GGAAAAGAAG AAGCACTAAT
8801 ATTGAAAAAC TTAGGTCAAT GGGATACTCA TTGACTGGAG CTGTGCAGAC
8851 CCTCTCACAA ATATCAGATA TAAATGATGA AAGACTTCAA CAAGGAGTTT
8901 ACTTATTGAG AGATCATGTT GTCACCTTAA TGGAAGCCGC CTTGCATGAT
8951 ATTACTATTA TGGAAGGAAT GTTAGCAATC GGTCATGTGC ATACCCACTT
9001 GAATCATCTT AAAACCATGT TACTAATGAG GAAGATTGAC TGGACTTTTA
9051 TTAAGAGTGA TTGGATTAAA GAACAACTTC AGAAAACTGA AGATGAAATG
9101 AAGATTATTA GAAGAACAGC TAAAAGTTTA GTATATTATG TGACTCAAAC
9151 ATCATCTTCC ACTACAGCAA CATCATGGGA AATTGGAATT TATTATGAAA
9201 TAACTATACC AAAACATATT TATTTGAATA ATTGGCAAGT TGTTAACATA
9251 GGTCATCTGA TTGAGTCAGC TGGTCATTTG ACCTTAATAA GGGTTAAACA
9301 TCCTTATGAA GACTTTAATA AAGAATGCAC ATATGAACAA TATTTACATC
9351 TTGAAGACTG CATATCTCAG GATTATGTGA TTTGTGACAC GGTACAAATA
9401 GTGTCACCAT GTGGAAACTC AACAGTAACC AGTGACTGCC CTGTCACTGC
9451 TGAAAAGGTA AAGGAACCAT ATATTCAAGT GTCAGCTTTA AAAAATGGAA
9501 GCTATTTGGT TCTAACCAGT AGAACAGATT GCTCAATACC AGCATATGTT
9551 CCCAGCATTG TAACTGTGAA CGAAACAGTT AAGTGTTTTG GGGTTGAGTT
9601 TCATAAACCA CTATACTCAG AAAGTAAAGT CAGCTTTGAA CCACAAGTTC
9651 CACATCTGAA ACTACGCTTG CCACATCTGG TTGGGATTAT TGCAAGTCTT
9701 CAAAATTTGG AAATTGAAGT AACCAGCACC CAAGAGAGTA TAAAAGATCA
9751 GATTGAAAGA GTTCAATCAC AGCTTCTTCG GCTGGACATT CACGAGGGAG
9801 ACTTTCCTGC TTGGATTCAA CAACTTGCTT CTGCAACCAA GGACGTCTGG
9851 CCTGCAGCTG CTAAAGCTCT TCAAGGCATA GGTAACTTTT TATCTAATAC
9901 TGCCCAGGGA ATATTTGGAA CTGCTGTAAG TATTCTATCC TATGCCAAGC
9951 CTATTCTTAT AGGAATAGGT GTTATACTTT TGATTGCATT CTTGTTTAAG
10001 ATTGTATCAT GGCTTCCTGG GAAGAAGAAA AAGAACTAGG ACATCTGCAT
10051 CTTCCAGAAG ACGATCCTCT GCCCAATTTA GATGTGCTCC TGGGTCTTGA
```

-continued

```
10101 TCATATGGAA TCCAATGAAG GACCTGATCA AAATCCAGGA GCTGAAAAGA
10151 TCTACATTCA ACTCCAAGCA GTCCCAGGGG AAGCCTCAGA GAAAACTTAC
10201 AAATTTGGAT ATGAAGACAA AGAGGCACAA AATCCTGACT TAAAAATGAG
10251 AAATTGGGTT CCTAACCCCG ACAAAATGAG TAAGTGGGCC TGTGCAAGGC
10301 TTATTCTTTG TGGACTTTAT AATGCAAAAA AGGCTGGAGA ACTCTTGGCT
10351 ATGGACTATA ATGTTCAATG GGAACAATCA AAAGAAGACC CAGGATACTT
10401 TGAAGTGGAA TATCACTGTA AAATGTGCAT GACTGTTATT CATGAACCTA
10451 TGCCTATCCA ATATGATGAA AAAACTGGAT TATGGCTAAA AATGGGTCCC
10501 CTTAGGGGAG ATATAGGATC TGTAGTACAT ACTTGTAGAA GGCATTACAT
10551 GAGATGTTTG TCTGCCCTTC CTAGCAATGG AGAACCTCTC AAACCTAGAG
10601 TCCGGGCTAA TCCTGTCCGA AGATATCGAG AGAAGCAAGA GTTCGTTGCG
10651 ACTAGGCCTA AACGCTCCAG ATGGGGTGTG GCCCCTAGCG CAGACTCCCA
10701 TACTTCCAGT GGTGACGCCA TGGCCCTTAT GCCAGGACCA TGCGGCCCCC
10751 TCGGTATGGA CACTCCTGGT TGCTTACTGG AAGGGATACA AGGATCAGGG
10801 CCTGGAACCT CCGAAATGGC TGTGGCAATG TCAGGAGGAC CTTTCTGGGA
10851 AGAAGTGTAT CGAGACTCAA TTCTTGGTGC CCCCACTGGG TCTAGTGAAA
10901 ATTAGGCTTT ATCAAAATCT AACTGTTGTA AATGTTTGTG GATCTGTTGA
10951 CCCATGGGAA AATGAGAATC CCACTAGAGG TCGCAGAGGG CCTATGCATA
11001 GATATGATTG TAGAATTGCT TGTGATCCAA GCTATTGCTT TAAGGCTATT
11051 TGGGAAGGAA ACTTTTGGGA CAAAAAAAAA AGGATCAGGC ATGCTGGCTA
11101 GTTCATCTGA AGAAGGACA TAAATTTGGT GCAGATGAGT TATCTTCTGG
11151 GGATCTTAAA ATATTAGCAG AATCTAGACC TTATCCATAT GGATCTATTG
11201 GTCATTGTGC TATGCTTCAA TATGCAGTAC AAGTTAAAAT GAGAGTTGAT
11251 AGAGCTCCTT TGACCTCAAA GGTGAGAGCT ATTAAAGCTT GCACTATCA
11301 TCGCTGGAAT ATTTGTCAGC TGGAAAATCC TGGCATAGGA GAGGGATTCA
11351 GTCCCTCTGG TAATACACAA GCTCTTAAAG CCTATGGACC TCAGCATGGA
11401 AGTGAAGAGG AGAGGGTGTG GCTGACAGCT ACTAAAATGA TTGGCACCCA
11451 GGAATCAGAC TATTGGCATG AGTACAAAAG ATGGGGATAT TTCCCTTTGA
11501 TTCCAAATAA ACATCATCCT GGGTGGACTA GACATCTTAC TAAATTCAAG
11551 ATATCTAGAT TCTCCACTCC TGCTGATGTC CAGAAAATTG TGGATGAGCT
11601 TCTCCCTAGA GGAGCAAGCA TTGTAATGCC AGATGGAACA AAGTATCCAA
11651 GTACCAGAAA AGTGCACTTA GTCAATGAAG GAACCCTTGT AGAATACCAA
11701 GCCAAATGTA AGGAGATAGA GGAAAAGTAC GGAGGATGCT TTTCTACAGA
11751 TAGTGATGAT GACAGTGATG ATTACTCTGA GGATACTCCA GAAACTGAAA
11801 CCACTGATGT GGAATAGAGT ACAGTGTTAA GGATTTACAT AATCTGCCTA
11851 GCAACTGCTT ATGCTTAAGA ATGAATCAGT ATATTGTTTA GGAATAAGCC
11901 TTAGTTTATA AGTAGTTAAT CCTTAGGGAG TATTTGGTGG AAATGACTGA
11951 GTGACATGAA GTTTATTCAC CATACTCTCA ATAGGAGCCA CTAGTTGAGC
12001 CTGTGCGTTC AAATCCATGC TCAGCTTAAG TGACTCCCTT TTAGTTTCAC
12051 TTTAAGTTAA GTTAGGAATA AGTTCCATAT AATCCTAAGG GAGTATGTGG
```

```
-continued
12101 ACCTTCTTGT TAGGAAATAG TTTAAGATAG TCCACAGCTC CCTTCTTTTT

12151 GAGTTCTAGT CTTTGTTAAG TTTGTTGGCT CATACAGATA AAGTGCTCAT

12201 TAAACAGGAA ACCGCAACCG GGTAAAGGTT AGCACAGTAA ATTAAGCTAG

12251 CAGTTACTCA AGAGCCCGGT AAGCATTCAA GTAGTTCGAA TCCCTTTAAT

12301 GCTGACGGAT TGCTCTTTAG TGAGGTGATG TAATCTGTTT TTGCAATCTG

12351 AAATGTGTGT TTGCACAGGA AGTTGTACAA GAAAGGGAAT GGCTAAACTT

12401 GTTACAGTTC GAACAAACAT TTAGCAATTT CCTTTGCTTT TGGAGTTCGA

12451 GCCTTGTACT TATACTTTGA GCATATGTAT TGTAACACCT AAGTATGGAA

12501 AAATCTCCAA GTATGAGTCA CGAGATGCTT GGCTCACTGC GTTGGACGAC

12551 TGGAAAGAAG CTTCAACAGT CGGGACAGCA TCTCGAAGAA GGCCTCCGGA

12601 ATGAAAGAGT GAAAAATGAA GTCTCCTCAT TCAGAGAGCC TTCTTTTAGA

12651 ATTTCAGGCA GAATAGAGTT TCCAATAGAA TAAACTTTTG TATTAGCAGA

12701 TAGATAGGAT ATATAATCTC TGCTTTAGAT TGTACGGGAG CTCACCACTA

12751 CTCGCTGCGT CGAGAGTGTT CGAGTCTCTC CAGGCTTGGT AAGATATAAA

12801 CTTTGGTATT CTCTGTATTC TTATGATCCA ATATTACTCT GCTTATAGAT

12851 TGTAATGGGC AATGGCAATG CTTTATCAAT GAATGATTTT ATGGTGAATT

12901 AAGTTCATAT ATGTTTTAAG AAGTTTAACA ATAAACCGAC TTAATTCGAG

12951 AACCAGATTT ATTAGTATTG TCTCTTTCTA TACTTTAAGT AAAGTGAAAG

13001 GAGTTGTATA TTAGCCTTGC TTATAAGAGC CATCTAGTGG TATAAGTGTG

13051 TACTACACTT ATCTAAA
```

Seq. IDs 1–5 can be used for all the molecular biological techniques known to those skilled in the art. Such uses include, but are not limited to, generation of probes and vectors containing the sequences, antisense sequences derived from such sequences, and proteins synthesized using the sequences. RNA and other nucleic acid derivatives are contemplated by the present invention.

Knowing the entire sequence of SFVHu-1, Seq, ID 5, allows for the deletion and insertion of exogenous genetic sequences for use of the virus in treatments such as gene therapy. Having the complete genomic sequence will allow for the creation of novel viral vectors for gene therapy, attenuated recombinant vaccines and live viral vectors for the treatment and prevention of diseases. These and other molecular biological and medical procedures and treatments are contemplated by the present invention.

The 5' sequenced region of SFVHu-1, shown in Seq ID 3, comprises the LTR (Long Terminal Repeat). In foamy viruses, the LTR aids in the replication of the virus. The LTR is transactivated by a virus-specific protein, and unlike related retrovirus, HIV (Human Immunodeficiency Virus), no human cellular transcription factors activate the virus. LTRs in retroviruses like HIV have conserved consensus sequences for cellular transcription factors.

According to sequence homology, SFVHu-1 Seq ID 3, the LTRs are stable. There has not been significant change in the sequence even after long passage in a human host. For gene therapy uses, this stability is very important. It also appears that the internal promoter, found in the 3' sequence, Seq ID 4, is also conserved. Thus, the transcriptionally important regions of SFVHu-1 are stable. This indicates that the virus is not acquiring human sequences that would cause it to possibly become virulent or at least cause disease in humans due to introduced mutations. SFVHu-1, because of this stability, is an excellent vector, vaccine or gene therapy agent for humans. This stability is surprising is light of the high instability of the LTR of the virus known as HFV, Human Foamy Virus. HFV was derived from a nasocarcinoma and is now believed not to be a human foamy virus, but a chimpanzee virus. The HFV LTR is unstable and has lots of deletions, thus making it an undesirable vector.

The foamy viruses are unique in that at the 3' end of the env gene there is an internal promoter, IP. ORF 1 codes for a transactivator protein, TAF. TAF activates IP. Once the virus infects the cell, a little TAF is made, this TAF activates the internal promoter IP, which then causes the virus to make lots of TAF. Once sufficient quantity of TAF is made, the TAF functions to initiate the promoter found in the 5' LTR.

ORF 2 has presently unknown function, though it is theorized that it is necessary for replication of the virus in vivo. Without all of ORF 2 present, the virus will replicate in vitro, but the existing paradigm, prior to the present invention, was that ORF 2 was required for in vivo replication. ORF 2 is a putative site for gene insertion. Surprisingly, it has been found in Seq. ID 4, that ORF 2 of SFVHu-1 has multiple stop codons that prevent its translation. SFVHu-1 has a 5 base insertion and a point mutation that prevent accurate translation of ORF 2. According to the existing theory for foamy virus replication in vitro discussed above, these mutation should prevent replication of SFVHu-1 in humans. Surprisingly, the inventors have found that SFVHu-1 has a high rate of replication in the human host. The virus is found in the peripheral blood lymphocytes (PBL) of the host and is cultured from such cells in tissue culture systems. Reverse transcriptase activity has been found in the PBLs and plasma of the infected host. Viral RNA of SFVHu-1 has been shown by viral RT-PCR in both PBLs and plasma of the infected host. No other foamy virus has shown this activity. The literature has reported that there has been no identification of foamy viral replication in humans, until now, with the present invention, no such replication has been shown.

Knowing the entire sequence for SFVHu-1, Seq. ID 5, allows for various uses of the virus and viral sequences. The env gene of SFVHu-1 is necessary for foamy virus entry into animal cells. The gene of the present invention is effective in permitting infection of cells in a human host. Thus, for example, the env gene is used for uptake of foreign DNA by a wide range of human cells. There has long been a need for vectors for getting foreign nucleic acids into cells, both in vivo and in vitro. The introduction of foreign or exogenous nucleic acids into cells has been a technological hurdle for many gene therapy applications and has now been solved by the virus and sequences of the present invention. The env sequences can be used with any vector known to those skilled in the art, and with any other genetic sequences of choice, to allow for entry of the nucleic acids into the cells.

In another embodiment of the present invention, sequences of the foamy virus of the present invention can be used for other molecular biological applications. Regions of the gag gene are important in packaging genetic material. For example, the gag sequence or regions of the sequence are incorporated into other vectors and direct the packaging of the resultant genetic material for the particular application desired, such as packaging recombinant sequences to make altered infectious virions. Regions of the pol gene are known to be critical for the stable integration of foreign/viral DNA into the host genome. Vectors comprising the pol gene sequences can be used to integrate any DNA into a genome. The foamy virus and sequences of the present invention infect human cells, and thus, these sequences are used with other foreign or exogenous sequences in humans in methods, including, but not limited to, entry into cells, packaging, and insertion into the genome. Additionally, methods of using the foamy virus and sequences of the present invention are not limited to human cells, but all cells that allow for infection or entry of the nucleic acids.

The present invention is directed to compositions and methods comprising a new spumavirus, SFVHu-1, particularly compositions and methods for the sequences of the viral genome. The virus was isolated from humans who had worked with nonhuman primates. The new spumavirus, or foamy virus, does not appear to cause any disease in the human hosts. The new virus of the present invention may be an excellent vector for gene therapy and for vaccination purposes. Additionally, the antibodies or other detection methods for detecting the new virus may be important in detecting the presence of this and related viruses for xenotransplantation. In addition, the novel spumavirus of the present invention can be used as a reagent in pathogenicity studies of these and related viruses. Moreover, the sequences of the novel spumavirus of the present invention can be used as probes to detect virus in biological samples. Vectors include but are not limited to prokaryotic, eucaryotic and viral vectors.

Many new and potentially useful technologies are being developed which use viral vectors and may form the basis of future medical cures and therapies. Examples of such technologies include, but are not limited to, gene replacement, antisense gene therapy, in situ drug delivery, treatment of cancer or infectious agents, and vaccine therapy. However, to be successful, these technologies require an effective means for the delivery of the genetic information across cellular membranes.

The recent advent of technology, and advances in the understanding of the structure and function of many genes makes it possible to selectively turn off or modify the activity of a given gene. Alteration of gene activity can be accomplished many ways. For example, oligonucleotides that are complementary to certain gene messages or viral sequences, known as "antisense" compounds, have been shown to have an inhibitory effect against viruses. By creating an antisense compound that hybridizes with the targeted RNA message of cells or viruses the translation of the message into protein can be interrupted or prevented. In this fashion gene activity can be modulated.

The ability to deactivate specific genes provides great therapeutic benefits. For example, it is theoretically possible to fight viral diseases with antisense molecules that seek out and destroy viral gene products. In tissue culture, antisense oligonucleotides have inhibited infections by herpesviruses, influenza viruses and the human immunodeficiency virus that causes AIDS. It may also be possible to target antisense oligonucleotides against mutated oncogenes. Antisense technology also holds the potential for regulating growth and development. However, in order for the gene therapy to work, antisense sequences must be delivered across cellular plasma membranes to the cytosol.

Gene activity is also modified using sense DNA in a technique known as gene therapy. Defective genes are replaced or supplemented by the administration of "good" or normal genes that are not subject to the defect. Instead of being defective, the gene have been deleted, thus replacement therapy would provide a copy of the gene for use by the cell. The administered normal genes can either insert into a chromosome or may be present as extracellular DNA and can be used to produce normal RNA, leading to production of the normal gene product. In this fashion gene defects and deficiencies in the production of a gene product may be corrected. Still further gene therapy has the potential to augment the normal genetic complement of a cell. For example, it has been proposed that one way to combat HIV is to introduce into an infected person's T cells a gene that makes the cells resistant to HIV infection. This form of gene therapy is sometimes called "intracellular immunization." Genetic material such as a polynucleotide sequence may be administered to a mammal in a viral vector to elicit an immune response against the gene product of the administered nucleic acid sequence. Such gene vaccines elicit an immune response in the following manner. First, the viral vector containing the nucleic acid sequence is administered to a human or animal. Next, the administered sequence is expressed to form a gene product within the human or animal. The gene product inside the human or animal is recognized as foreign material and the immune system of the human or animal mounts an immunological response against the gene product. The virus of the present invention may be used as a viral vector to provide the foreign nucleic acid sequences to the intracellular metabolic processes.

Additionally, gene therapy may be used as a method of delivering drugs in vivo. For example, if genes that code for therapeutic compounds can be delivered to endothelial cells, the gene products would have facilitated access to the blood stream. Additionally, cells could be infected with a retroviral vector such as the present invention carrying nucleic acid sequences coding for pharmaceutical agents that prevent infection from occurring in the retrovirally infected cells.

The novel spumavirus of the present invention can also be used a safe and effective vaccine agent. Genetic sequences for immunogenic proteins from a variety of infectious agents can be incorporated into the foamy virus RNA. Once inside a cell, the gene product is expressed and releases the immunizing peptide to the body's immune system. In another method, the virus of the present invention can be used to immunize the body against cell markers found on cancer or tumor cells. The genetic sequence of the cancer cell marker is incorporated into the foamy virus RNA and after infection with the virus, the expressed gene product stimulates the immune system. The patient's immune system is used to remove the cancerous cells, obviating the need for chemotherapeutic methods.

The antibodies of the present invention can be used to detect the presence of the virus or viral particles of the present invention. These antibodies can be used in diagnostic or screening kits to assess the present of the virus. Additionally, the antibodies can be used to screen organs from nonhuman primates that may be used in humans. Detection of the presence of a virus that is transmitted from nonhuman primates to humans would be crucial in providing virus-free organs for transplantation.

The virus of the present invention can be used for the treatment of conditions due to the presence of rapidly dividing cells. In a host, the ability of SFVHu-1 to productively infect dividing cells provides an excellent treatment for conditions due to the presence of rapidly dividing cells. For example, a person with disease due to rapidly dividing cells, including but limited to cancer or any known angiogenic condition, could be infected with SFVHu-1. Such virus may or may not carry other, exogenous genes for other effects in the host. Because SFVHu-1 does not cause disease in the host and there is no transmission of the virus to contacts with the host, only the person with the condition due to rapidly dividing cells will be treated. In addition, only the rapidly dividing cells of that host person will be productively infected by SFVHu-1. Other cells in the body may be infected but will not be killed because the infection in nondividing cells is not productive. The virus will productively infect the rapidly dividing cells and kill them. For example, a person with a fast growing tumor would be infected with SFVHu-1 and the cells of the tumor would be destroyed by the virus. Additionally, the virus may be given to a person prior to the person developing a condition caused by dividing cells, and when the cells begin dividing, the virus would then undergo a productive infection and kill the cells. This therapy may halt or inhibit such conditions as leukemia or angiogenesis dependent diseases such as macular degeneration.

Such treatment with SFVHu-1 could be used for any condition in which rapidly dividing cells provide an aspect of the pathology of the condition. One such condition is the presence of uncontrolled angiogenesis within the body. Angiogenesis dependent diseases are well known in the art and are caused in part by the rapid growth of blood vessels. Another such condition is cancer or tumor growth. Cancer or tumors include both solid tumors and other types. Infection with the virus of the present invention, which causes no disease and does not effect the host systemically, is an improvement over currently known treatments that involved systemically administered agents. Such chemotherapeutic agents kill rapidly dividing cells but also cause trauma to the entire person. The dosages of such chemotherapeutic agents must be titered between killing the cancer and killing the patient.

In contrast, treatments of cancer with the present invention are not as harmful to the patient. The virus can either be administered systemically or injected in situ into the tumor. The virus will only replicate in rapidly dividing cells and will not effect cells that are not dividing. The infected cells are killed and tumor growth is stopped. The virus may be administered in one treatment or in a series of treatments.

The SFVHu-1 of the present invention can be recombinantly modified to be selective for cellular receptors on the tumor to make the virus even more specifically targeted to just those cells. Additionally, the virus may have altered promoter regions that can be selectively activated to cause a productive infection. The combination of different levels of control of the virus, both natural and recombinantly produced, are contemplated in the present invention. A virus could be made specific for attachment to only certain types of cellular receptors, for those cells that are dividing, and will only undergo replication if another exogenous promoter factor is present. Viral infection by two or more individually defective viruses, that require factors or promoters supplied by other foamy viruses or any type of virus, could provide for many levels of control of infection or treatment of specific conditions.

The virus may be administered to the host, for cancer treatment, gene therapy or vaccination by any methods known to those skilled in the art. Such methods include but are not limited to injection, inhalation, ingestion, topical administration and implantation. The virus may be killed or live, depending on the treatment considered.

The inventors of the present invention believe that the viruses of the present invention, comprising the isolates from Cases A, B, and C, and particularly Case A, are the first definitive isolation of an SFV-3-like spumavirus from persons exposed to nonhuman primates. The virus does not appear to cause disease and does not appear to be transmitted to close household contacts or sexual contacts. This belief is supported by the epidemiology data, the PCR and sequencing data and the serology data.

The isolate from Case A, SFVHu-1, was deposited with the ATCC under the Budapest Treaty on Feb. 5, 1998, and was assigned ATCC no. VR-2596.

The present invention is further described by the examples which follow. Such examples, however, are not to be construed as limiting in any way either the spirit or scope of the present invention. In the examples, all parts are parts by weight unless stated otherwise.

EXAMPLE 1

Case A

Case A has intermittently been employed as a caretaker for non-human primates for twenty years between 1961 and 1997. Case A recalled multiple minor injuries and mucocutaneous exposures to non-human primate blood, body fluids, or fresh tissue. In addition, Case A was twice bitten by African green monkeys in the 1960s or early 70s. These injuries were severe enough to require 7–10 stitches each. Case A is single and in good health. No sera collected from Case A prior to 1995 or from sexual partners are currently available for testing. Retrospective analysis of sera archived from Case A in 1995 showed the sera to have antibodies to SFV. (See FIG. 3, lane 2).

The western blot of FIG. 3 shows whole cell lysate from Cf2Th cells infected with the spumavirus of the present invention tested in each individual lane with different antisera. In FIG. 3, particular viral proteins that show infection are the proteins with molecular weight of approximately 70–80 Daltons (p70 gag protein) and the proteins at approximately 130–140 Daltons (an envelope protein). The western blot of FIG. 3 shows whole cell lysate from Cf2Th cells infected with the spumavirus of the present invention. These proteins are not detectable in the western blot of FIG. 3 by normal sera, (lane 1) but are detectable by antisera from Case A.

EXAMPLE 2

Case B

Case B is a research scientist employed for three decades working with biologic specimens from non-human primates. Case B rarely reported injuries involving non-human primate blood, body fluids, or unfixed tissue, but did report an injury in 1970 when an unused needle was stuck through a glove that was potentially contaminated with baboon body fluids; and a 1972 cut inflicted by a broken capillary tube containing chimpanzee blood. Case B is in good health. Case B has been in a monogamous sexual relationship without use of barrier contraceptives or spermicides for over 20 years. Case B's spouse is negative for SFV-like infection by both serologic and PCR testing. Analysis of two serum specimens from Case B archived serially in 1967 were negative; sera archived in 1978 and subsequently were consistently seropositive. See FIG. 3, lanes 3 and 4 are the 1967 sera, lane 5 is sera from 1978, lane 6 is sera from 1980, lane 7 is sera from 1981. The sera of Case B's spouse is shown in lane 10.

EXAMPLE 3

Case C

Case C is an animal care supervisor who has worked with non-human primates for more than 3 decades. Case C recalls multiple minor injuries and mucocutaneous exposures to non-human primate blood, body fluids, or unfixed tissues. Case C reported a severe baboon bite around 1980 that required multiple stitches of an arm and hand. Case C is in good health except for type II diabetes mellitus. Case C has been in a monogamous sexual relationship for nearly three decades, during which barrier methods of contraception have not been employed and spermicides were used for no more than a 6 month period. Case C's spouse is negative for SFV-like infection by both serologic and PCR testing. Retrospective analysis of sera archived from Case C in 1988 showed the sera to have antibodies to SFV. See FIG. 3, lane 8 is Case C's sera from 1988, and lane 11 is sera from the spouse of Case C.

EXAMPLE 4

Western Blot Analysis

Figure 3:
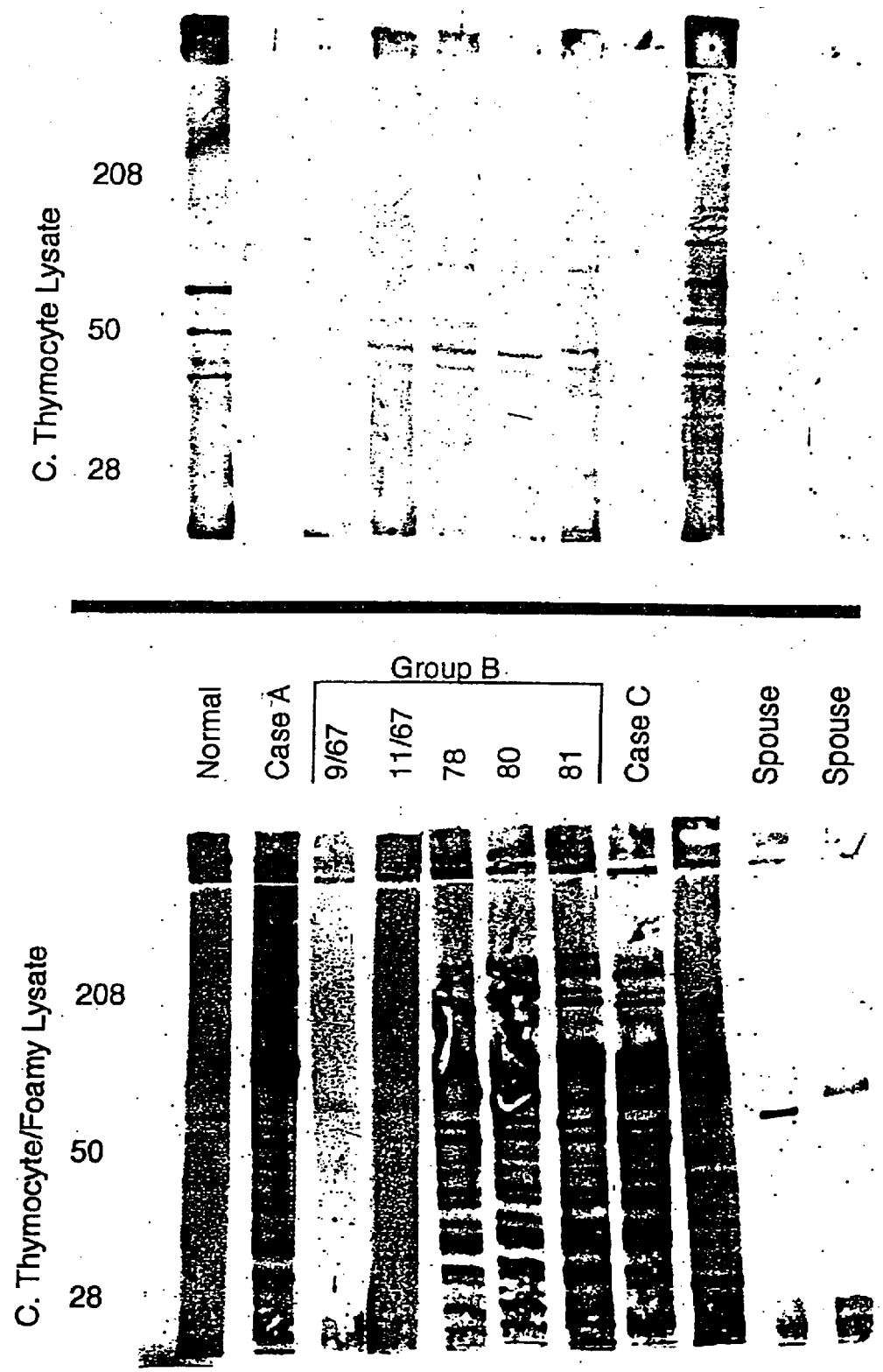
Figure 4:
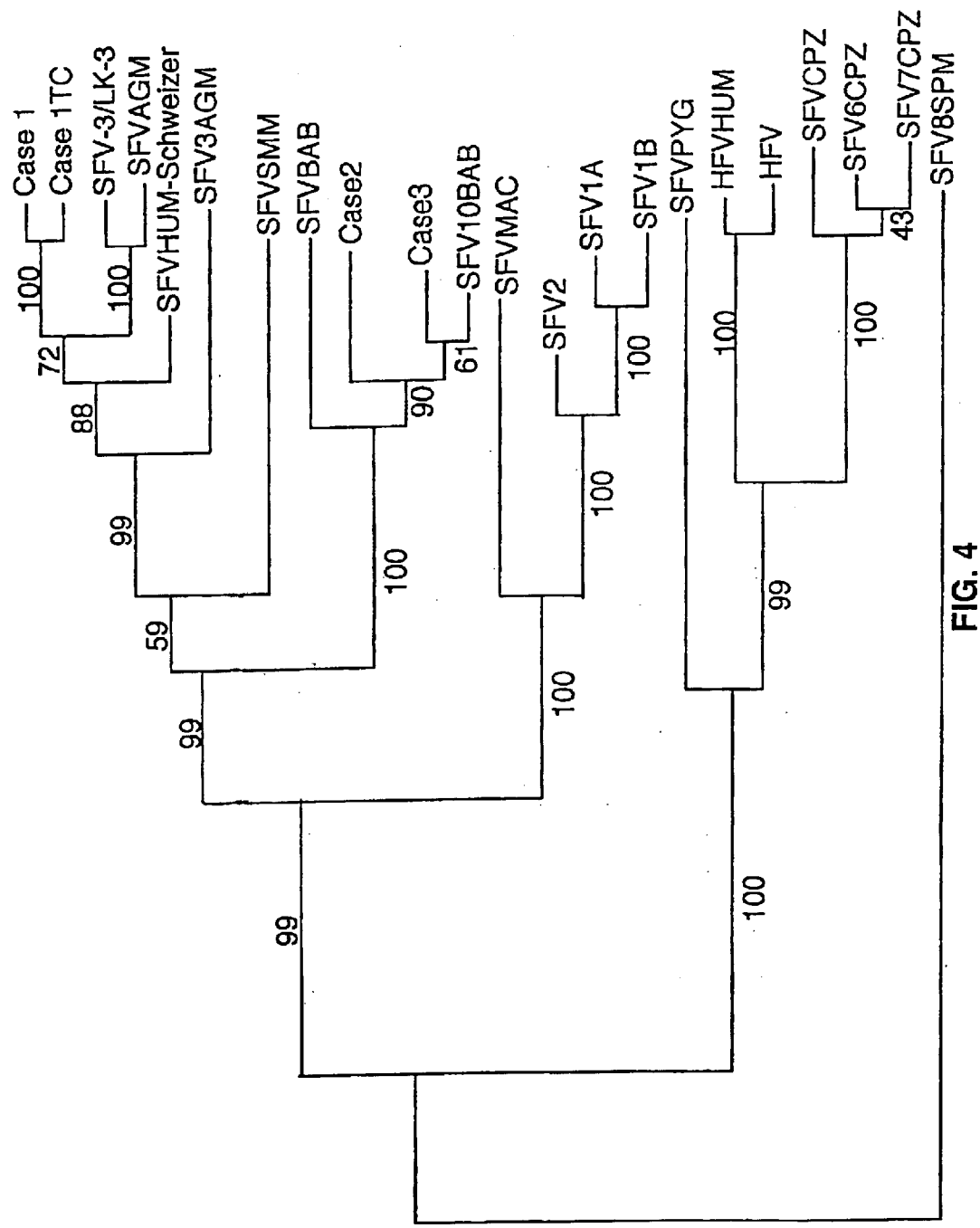

The sera from the three cases were analyzed by western blot analysis against whole cell lysates from Ct2Th cells infected by cell free supernatants from Ct2Th cells infected by a Case's PBLs. As shown in FIG. 3, Case A, Case B and Case C all show the characteristic gag proteins associated with the spumavirus. It is interesting to note that in Case B, Case B converted from negative to positive between 1967 and 1978. In addition, spouses of two of the Cases were negative.

EXAMPLE 5

Simian Foamy Virus Isolation

Peripheral blood lymphocytes (PBLs) were isolated from Cases A, B and C and were cultured with IL-2 for 48 hours, in RPI media with 10% fetal Calf serum, and penn-strep antibiotics. After 48 hours, the PBLs were added to the Cf2Th cells and co-cultured for 2–4 weeks. The cells were in DMEM supplemented with 2% nonessential amino acids, 20% fetal calf serum, and pen-strep antibiotics. 1 mL supernatants were collected from the cell cultures every 3 to 4 days and tested for amp-reverse transcriptase. Procedures for PBL treatment, culturing of Cf2Th cells and amp reverse transcriptase activity were procedures known to those in the art. For example, see Heneine, W., et al. "Detection of reverse transcriptase by a highly sensitive assay in sera from persons infected with HIV-1." (1995). J. Infectious Diseases, 171:1201–6.

EXAMPLE 6

Because of the positive amp-reverse transcriptase activity from cells from Case A, peripheral blood lymphocytes from Case A were cultured with IL-2 for 48 hours prior to addition to canine thymocytes (Cf2Th), human lung fibroblasts, and normal human peripheral blood lymphocytes. Supernatants were collected every 3 to 4 days and tested for amp-reverse transcriptase activity. Each time the 1 mL sample of supernatant was taken for amp-reverse transcriptase activity, a 5 mL sample of supernatant was taken and frozen at −80° C. in order to preserve a sample of the virus producing the amp-reverse transcriptase activity.

Figure 2:
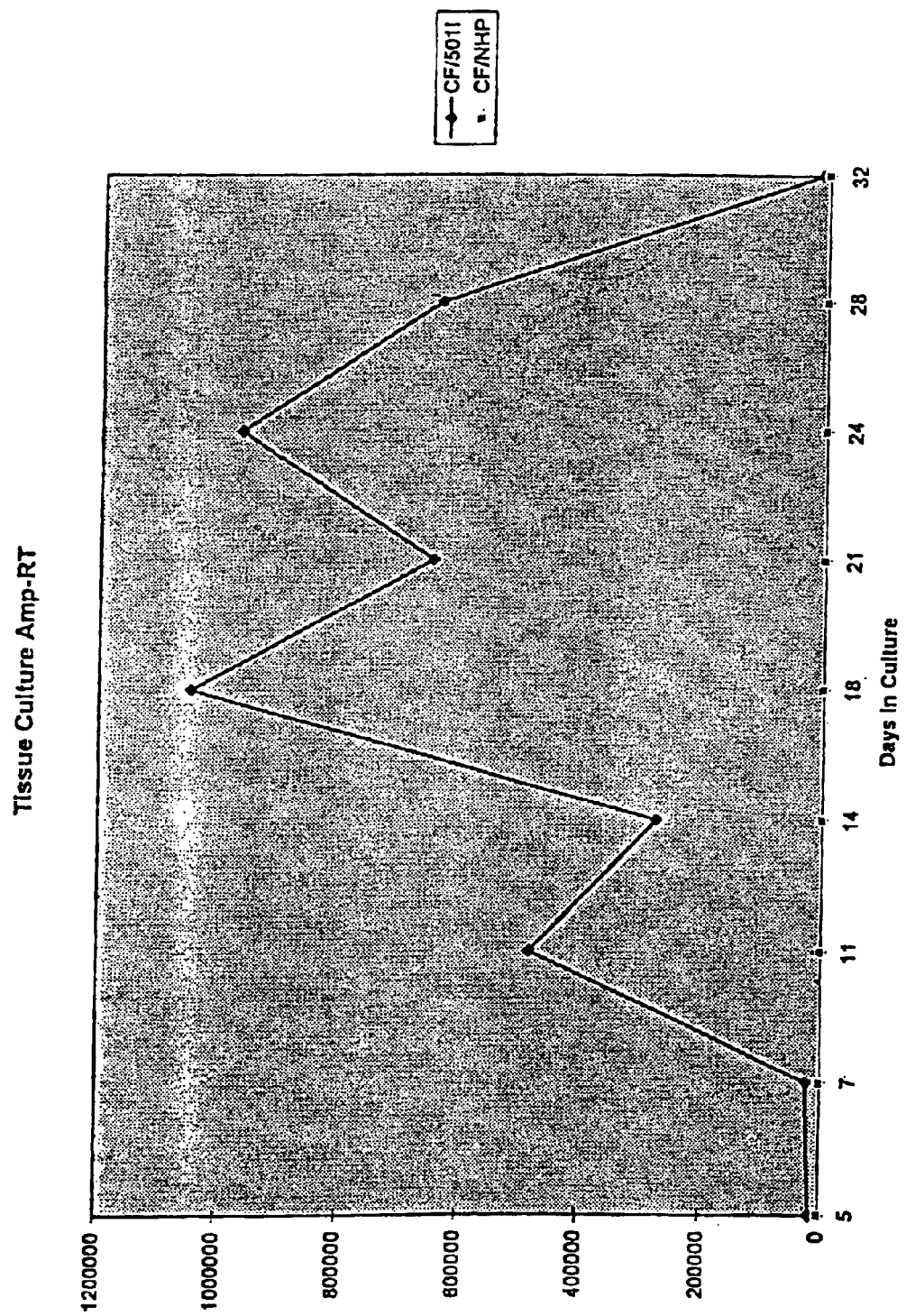

At day 5, amp-reverse transcriptase testing showed a slightly positive signal in the canine thymocyte culture. The amp-reverse transcriptase activity increased over time. (See FIG. 2).

The activity in control Cf2Th cells that were treated as above, except for exposure to normal PBLs instead of infected PBLs, was shown by the lower line that overlaps the baseline. There was no amp-reverse transcriptase activity inherently in these Cf2Th cells, providing evidence that there was no contamination by a retrovirus or spumavirus by the tissue culture cells.

EXAMPLE 7

At the peak of amp-reverse transcriptase activity as described in Example 5, cell-free supernatants were transferred to fresh Cf2Th growing at $2 \times 10^5$ cells/mL. At day 4 in the new culture, cytopathic effects and syncytia were observed. Transmission electron microscopy showed viral particles in and around the cells (See FIG. 1). Viral particles were isolated from these cultures and were stored at the Centers for Disease Control and were deposited at the ATCC.

The Cf2Th cells were obtained from the in-house cell culture facility of the Centers for Disease Control, but these cells can also be obtained from the American Type Culture Collection (Rockville, Md.). See Mergia et al., et al., "Cell tropism of the simian foamy virus type 1 (SFV-1)," J. Med. Primatol. 1996:25:2–7, for use of these cells.

Having thus described the invention, numerous changes and modifications thereof will be readily apparent to those having ordinary skill in the art, without departing from the spirit or scope of the invention.

SEQUENCE LISTING

<160> NUMBER OF SEQ ID NOS: 5

<210> SEQ ID NO 1
<211> LENGTH: 423
<212> TYPE: DNA
<213> ORGANISM: Human foamy virus

<400> SEQUENCE: 1

```
ttactacaag gacaatatcc aaaaggtttt ccaaaacaat atcaatatga acttaatgaa      60
ggacaagtta tagtaactcg tcctaatgga caaagaatta ttcctccaaa atcagacagg     120
cctcaaatta ttttgcaagc acataatatt gcacatacag gaagagattc aacctttctt    180
aaggtctctt ccaagtattg gtggccaaat cttagaaagg atgtggttaa agttatcaga    240
caatgtaagc aatgtctggt cacaaatgca gctaccttag ctgcgcctcc aatactgagg    300
cctgaaagac ctgtaaagcc ttttgataaa tttttgttg actatattgg ccctttaccc    360
ccttctaatg ggtacttaca tgtccttgta gtagtcgatg gtatgactgg atttgtatgg    420
tta                                                                    423
```

<210> SEQ ID NO 2
<211> LENGTH: 423
<212> TYPE: DNA
<213> ORGANISM: Human foamy virus

<400> SEQUENCE: 2

```
ttactacaag gacaatatcc aaaaggtttt ccaaaacaat atcaatatga acttaatgaa      60
ggacaagtta tagtaactcg tcctaatgga caaagaatta ttcctccaaa atcagacagg     120
cctcaaatta ttttgcaagc acataatatt gcacatacag gaagagattc aacctttctt    180
aaggtctctt ccaagtattg gtggccaaat cttagaaagg atgtggttaa agttatcaga    240
caatgtaagc aatgtctggt cacaaatgca gctaccttag ctgcgcctcc aatactgagg    300
cctgaaagac ctgtaaagcc ttttgataaa tttttgttg actatattgg ccctttaccc    360
ccttctaata ggtacttaca tgtccttgta gtagtcgatg gtatgactgg atttgtatgg    420
tta                                                                    423
```

<210> SEQ ID NO 3
<211> LENGTH: 1567
<212> TYPE: DNA
<213> ORGANISM: Human foamy virus

<400> SEQUENCE: 3

```
ttcccaataa acatcatcct gggtggacta gacatcttac taaattcaag atatctagat      60
tctccactcc tgctgatgtc cagaaaattg tggatgagct tctccctaga ggagcaagca    120
ttgtaatgcc tgatggaaca agtatccaa gtaccagaaa agtgcactta gtcaatgaag     180
gaacccttgt agaataccaa gccaaatgta aggagataga ggaaaagtac ggaggatgct    240
tttctacaga tagtgatgat gacagtgatg attactctga ggatactcca gaaactgaaa    300
ccactgatgt ggaatagagt acagtgttaa ggattcacat aatctgccta gcaactgctt    360
atgcttaaga atgaatcagt atattgttta ggaataagtt atagtttata gaagttaat     420
ccttagggag tatttggtgg aaatgactga gtgacatgaa gtttattcac catactctca    480
ataggagcca ctagttgagc ctgtgcgttc aaatccatgc tcagcttaag tgactccctt    540
ttagtttcac tttaagttaa gttaggaata agttccatat aatcctaagg gagtatgtgg    600
```

-continued

```
accttcttgt taggaaatag tttaagatag tccacagctc ccttcttttt gagttctagt      660
ctttgttaag tttgttggct catacagata aagtgctcat aaacaggaa accgcaaccg       720
ggtaaaggtt agcacagtaa attaagctag cagttactca agagcccggt aagcattcaa      780
gtagttcgaa tcccttttaat gctgacggat tgctctttag tgaggtgatg taatctgttt    840
ttgcaatctg aaatgtgtgt ttgcacagga agttgtacaa gaaagggaat ggctaaactt     900
gttacagttc gaacaaacat ttagcaattt cctttgcttt tggagttcga gccttgtact    960
tatactttga gcatatgtat tgtaacacct aagtatggaa aaatctccaa gtatgagtca   1020
cgagatgctt ggctcactgc gttggacgac tggaaagaag cttcaacagt cgggacagca   1080
tctcgaagaa ggcctccgga atgaaagagt gaaaaatgaa gtctcctcat tcagagagcc   1140
ttctttttaga atttcaggca gaatagagtt tccaatagaa taaacttttg tattagcaga  1200
tagataggat atataatctc tgctttagat tgtacgggag ctcaccacta ctcgctgcgt   1260
cgagagtgtt cgagtctctc caggcttggt aagatataaa ctttggtatt ctctgtattc   1320
ttatgatcca atattactct gcttatagat tgtaatgggc aatggcaatg ctttatcaat  1380
gaatgatttt atggtgaatt aagttcatat atgttttaag aagtttaaca ataaaccgac   1440
ttaattcgag aaccagattt attagtattg tctctttcta tactttaagt aaagtgaaag   1500
gagttgtata ttagccttgc ttataagagc catctagtgg tataagtgtg tactacactt   1560
atctaaa                                                               1567
```

<210> SEQ ID NO 4
<211> LENGTH: 2408
<212> TYPE: DNA
<213> ORGANISM: Human foamy virus
<220> FEATURE:
<221> NAME/KEY: misc_feature
<222> LOCATION: (763)..(763)
<223> OTHER INFORMATION: "n" = unknown
<220> FEATURE:
<221> NAME/KEY: misc_feature
<222> LOCATION: (782)..(782)
<223> OTHER INFORMATION: "n" = unknown

<400> SEQUENCE: 4

```
aagggatgt tgagcaatcc aacatgtgca tacccacttg aatcatctta aaaccatgtt      60
actaatgagg aagattgact ggactttat taagagtgat tggattaaag aacaacttca     120
gaaaactgaa gatgaaatga agattattag aagaacagct aaaagtttag tatattatgt    180
gactcaaaca tcatcttcca ctacagcaac atcatgggaa attggaattt attatgaaat   240
aactatacca aaacatatttt atttgaataa ttggcaagtt gttaacatag gtcatctgat   300
tgagtcagct ggtcatttga ccttaataag ggttaaacat cctttatgaag actttaataa   360
agaatgcaca tatgaacaat atttacatct tgaagactgc atatctcagg attatgtgat   420
ttgtgacacg gtacaaatat tgtcaccatg tggaaactca acagtaacca gtgactgccc   480
tgtcactgct gaaaaggtaa aggaaccata tattcaagtg tcagctttaa aaaatggaag   540
ctatttggtt ctaaccagta gaacagattg ctcaatacca gcatatgttc ccagcattgt   600
aactgtgaac gaaacagtta agtgttttgg ggttgagttt cataaaccac tatactcaga   660
agtaaagtc agctttgaac cacaagttcc acatctgaaa ctacgcttgc cacatctggt    720
tgggattatt gcaagtcttc aaaatttgga aattgaagta acnagcaccc aagagagtat   780
anaagatcag attgaaagag ttcaatcaca gcttcttcgg ctggacattc acgagggaga    840
```

```
ctttcctgct tggattcaac aacttgcttc tgcaaccaag gacgtctggc ctgcagctgc      900
taaagctctt caaggcatag gtaacttttt atctaatact gcccagggaa tatttggaac      960
tgctgtaagt attctatcct atgccaagcc tattcttata ggaataggtg ttatactttt     1020
gattgcattc ttgtttaaga ttgtatcatg gcttcctggg aagaagaaaa agaactagga     1080
catctgcatc ttccagaaga cgatcctctg cccaatttag atgtgctcct gggtcttgat     1140
catatggaat ccaatgaagg acctgatcaa atcccaggag ctgaaaagat ctacattcaa     1200
ctccaagcag tcccagggga agcctcagag aaaacttaca aatttggata tgaagacaaa     1260
gaggcacaaa atcctgactt aaaaatgaga aattgggttc ctaaccccga caaaatgagt     1320
aagtgggcct gtgcaaggct tattctttgt ggactttata tgcaaaaaa ggctggagaa     1380 ctcttggcta tggactataa tgttcaatgg gaacaatcaa aagaagaccc aggatacttt     1440
gaagtggaat atcactgtaa aatgtgcatg actgttattc atgaacctat gcctatccaa     1500
tatgatgaaa aaactggatt atggctaaaa atgggtcccc ttaggggaga tataggatct     1560
gtagtacata cttgtagaag gcattacatg agatgtttgt ctgcccttcc tagcaatgga     1620
gaacctctca aacctagagt ccgggctaat cctgtccgaa gatatcgaga gaagcaagag     1680
ttcgttgcga ctaggcctaa acgctccaga tggggtgtgg ccccctagcgc agactcccat     1740 acttccagtg gtgacgccat ggcccttatg ccaggaccat gcggccccctt cggtatggac     1800 actcctggtt gcttactgga agggatacaa ggatcagggc ctggaacctc gaaatggct     1860 gtggcaatgt caggaggacc tttctgggaa gaagtgtacc gggactcaat tcctggtgcc     1920
cccactgggt ctagtgaaaa ttaggcttta tcaaaatcta actgttgtaa atgtttgtgg     1980
atctgttgac ccatgggaaa atgagaatcc cactagaggt cgcagagggc ctatgcatag     2040
atatgattgt agaattgctt gtgatccaag ctattgcttt aaggctattt gggaaggaaa     2100
cttttgggac aaaaaaaaaa ggatcaggca tgctggctag ttcatctgaa agaaggacat     2160
aaatttggtg cagatgagtt atcttctggg gatcttaaaa tattagcaga atctagacct     2220
tatccatatg gatctattgg tcattgtgct atgcttcaat atgcagtaca agttaaaatg     2280
agagttgata gagctccttt gacctcaaag gtgagagcta ttaaagcttt gcactatcat     2340
cgctggaata tttgtcagct ggaaaatcct ggcataggag aaggattcag tccctctggt     2400
aatacaca                                                             2408
```

<210> SEQ ID NO 5
<211> LENGTH: 13067
<212> TYPE: DNA
<213> ORGANISM: Human foamy virus
<220> FEATURE:
<221> NAME/KEY: misc_feature
<222> LOCATION: (6670)..(6670)
<223> OTHER INFORMATION: "n" = unknown
<220> FEATURE:
<221> NAME/KEY: misc_feature
<222> LOCATION: (7803)..(7803)
<223> OTHER INFORMATION: "n" = unknown

<400> SEQUENCE: 5

```
tgtggctgac agctactaaa atgattggca cccaggaatc agactattgg catgagtaca       60
aaagatgggg atatttccct ttgattccaa ataaacatca tcctgggtgg actagacatc      120
ttactaaatt caagatatct agattctcca ctcctgctga tgtccagaaa attgtggatg      180
agcttctccc tagaggagca agcattgtaa tgccagatgg aacaaagtat ccaagtacca      240
gaaaagtgca cttagtcaat gaaggaaccc ttgtagaata ccaagccaaa tgtaaggaga      300
```

-continued

```
tagaggaaaa gtacggagga tgcttttcta cagatagtga tgatgacagt gatgattact    360
ctgaggatac tccagaaact gaaaccactg atgtggaata gagtacagtg ttaaggattt    420
acataatctg cctagcaact gcttatgctt aagaatgaat cagtatattg tttaggaata    480
agccttagtt tataagtagt taatccttag ggagtatttg gtggaaatga ctgagtgaca    540
tgaagtttat tcaccatact ctcaatagga gccactagtt gagcctgtgc gttcaaatcc    600
atgctcagct taagtgactc ccttttagtt tcactttaag ttaagttagg aataagttcc    660
atataatcct aagggagtat gtggaccttc ttgttaggaa atagtttaag atagtccaca    720
gctcccttct ttttgagttc tagtctttgt taagtttgtt ggctcataca gataaagtgc    780
tcattaaaca ggaaaccgca accgggtaaa ggttagcaca gtaaattaag ctagcagtta    840
ctcaagagcc cggtaagcat tcaagtagtt cgaatccctt taatgctgac ggattgctct    900
ttagtgaggt gatgtaatct gttttttgcaa tctgaaatgt gtgtttgcac aggaagttgt    960
acaagaaagg gaatggctaa acttgttaca gttcgaacaa acatttagca atttcctttg   1020
cttttggagt tcgagccttg tacttatact ttgagcatat gtattgtaac acctaagtat   1080
ggaaaaatct ccaagtatga gtcacgagat gcttggctca ctgcgttgga cgactggaaa   1140
gaagcttcaa cagtcgggac agcatctcga agaaggcctc cggaatgaaa gagtgaaaaa   1200
tgaagtctcc tcattcagag agccttcttt tagaatttca ggcagaatag agtttccaat   1260
agaataaact tttgtattag cagatagata ggatatataa tctctgcttt agattgtacg   1320
ggagctcacc actactcgct gcgtcgagag tgttcgagtc tctccaggct tggtaagata   1380
taaactttgg tattctctgt attcttatga tccaatatta ctctgcttat agattgtaat   1440
gggcaatggc aatgctttat caatgaatga ttttatggtg aattaagttc atatatgttt   1500
taagaagttt aacaataaac cgacttaatt cgagaaccag atttattagt attgtctctt   1560
tctatacttt aagtaaagtg aaaggagttg tatattagcc ttgcttataa gagccatcta   1620
gtggtataag tgtgtactta cacttatcta aagaggtgga attctttaag gataaccaat   1680
atacaaaatt ccacgacaat tggcgcccaa cgtggggctc gaatataagt cgggttttat   1740
tataaagact tgtttaagtc ttagaattat ccctagggac cttcacgcac tgcggaaggt   1800
ataagtactc aaagatgggt gatcataatt tgaatgttca agaactcttg aacctttttc   1860
agaatctagg tatttccaga caaccaaatc atagagaagt crtaggactt cgtatgacag   1920
gaggctggtg gggtccaggg acccgctata atctagtttc aatctttta caagatgatt   1980
ctggacaacc tttacaacaa cccaggtgga gacctgaagg tagaccagtt aatcctttgg   2040
ttcataatac tatagaagcc ccttggggag acttaaggtt agcttttgaa gacttggatg   2100
tagcagaagg tactttgagg tttggtcctt tagctaatgg aaattggatt cctggagatg   2160
aatactccat ggaattccag cctccactag cacaagaaat agctcaatta caaagagacg   2220
aaatggaaga atattggat ataacaggac aaatatgtgc acaagttata gatttagtag   2280
atatgcaaga tgctcaaatt agaggccytg aaagacgttt acaagataga ccaggtttaa   2340
gggataactt accagttgct ggtatacaag caccaccatc tagtccaatt gggcagccta   2400
ttgcatcatc ttcacttcaa cctgttcctg gatccagcca atcctctgct gatcttggtt   2460
gggaatcagg agcgcctggg caaatagatc ctagattgtc cagggtggcc tataacccat   2520
ttttaccagg accaagtgat gggtctgggg gatcaatccc agtccagcct agtgctcctc   2580
cagcggttct tccatcctta ccctcacttc ctgcacctgt tgctcaacct gttgttcagt   2640
```

```
atgttgttcc acctgcccct gctccacaag ctattccaat tcaacacatt cgagcagtga    2700
caggaaatac acctactaat ccaagagata ttcctatgtg gcttggaaga cattcagctg    2760
ctatagaagg agtatttcct atgactacgc ctgatcttcg ctgtcgagtt gttaatgctc    2820
ttataggagg aagtcttgga ctttctttgg agcctataca ttgtgtaaat tgggctgctg    2880
ttgtagctgc tctatatgtg agaacacatg gatcatatcc catacatgaa ctagctaatg    2940
tactccgagc agttgttaat caagagggag tagcaacagg ttttcaactt ggaattatgc    3000
tgtccaatca agattttaat cttgtttggg gaattctacg tcccctattg cctggacaag    3060
ctgtagtcac agctatgcag caaaracttg atcaagaagt cagtgacgct gctaggattg    3120
cctcctttaa tggacattta aatgatatat atcaacttct aggactgaat gcccgaggtc    3180
aaagcattac tagaactcag ggtagttcaa tctctggaac ctctacttct acaggcagag    3240
gaaggagagg acaaagaaac cagcaacagt ctggtcaaca gcaacaacaa caggcaagaa    3300
gaagtaatca gggaaaccag agacagagaa ataataatca gagacaatcc tctggtaata    3360
atcagggaca aggaggccaa ggaggatata atttgagacc cagaacttat cagccgcagc    3420
gctacggagg aggacgtgga agaagatgga acgataatca acaacagcaa caagcacagc    3480
caggcagatc agctgatcaa cctcgttccc agagtcagca accacaaaca gaggctcgtg    3540
gcgatcagtc acgaacatct ggtgctgggc gcggacaaca aggargaggg aaccaaaacc    3600
gaaatcaacg ccgggctgat gctaacaata ctcggaatgt ggatactgtg acagtaacca    3660
caacttcctc ctcccaaact ggttcgggtc aaaatggatc ctctacagct cctccagccc    3720
ctggaagcag aaatcaaggg gactaaatta aaggctcatt gggacagtgg agctacagta    3780
acatgtgttc cacaagcctt tctagaagat gaagtaccaa ttaaaaatat ttggatcaag    3840
acaattcatg gtgaaaaaga acagcctgtc tattatttaa cctttaaaat mcaaggaaga    3900
aaagtagaag cagaagtaat ctcttcccct tatgactaca tattagtcag tccatctgac    3960
atcccctggc taatgaagaa acctctccaa ttgacaactt tagttcctct tcaagaatac    4020
aaagaaagac ttttaaagca aactatttta actgaaaaat ataaagatag attacaatct    4080
ttatttttga aatatgatgc attatggcaa cattgggaaa atcaagtggg ccataggcgt    4140
attaagcctc atcatatagc aactggtaca gttaaccta gaccacaaaa gcaatatcca    4200
attaatccaa aagcaaagcc aagtatacaa gttgtaatta atgatttatt aaaacaaggt    4260
gtgctaatac agcaaaatag tgtgatgaat actcctgtat atcctgtacc aaaaccagat    4320
ggaaaatgga gaatggtttt agattataga gaagtcaata agaccatccc tttaattgca    4380
gctcaaaatc aacattctgc agggattcta tcatccatat ttagaggcaa atataaaacc    4440
actttagatt tatctaatgg ttttggggct cattctatta caccagaatc ttattggtta    4500
actgctttta cttggcttgg acaacaatat tgttggacaa gattacctca aggatttctc    4560
aatagtcctg ctttatttac agcagatgtt gttgatttat aaaagaagt accaaatgta    4620 caagtttatg tggatgatat ttatattagt catgatgacc ctgaagaaca tttggaccaa    4680
cttgagaaag tgttttcgct attgctcaaa tgcggttatg gggtttctct taaaaaatct    4740
gaaattgctc aacatgaagt tgaattcctt gggtttaata ttacaaaaga aggtcgaggc    4800
ctaacagaaa cttttaaaca aaaactctta aatataactc caccaaaaga tctgaaacag    4860
ttacaaagta ttttaggcct tctaaatttt gcaaggaact tgttcctaa ttttttctgaa    4920 ttagttaaac ccttatataa tatcattgct aatgccaatg agaaatatat tacatggact    4980
tctgacaata gtcaacagct acaatatata atttcattat taaattctgc agaaaactta    5040
```

```
gaagaaagaa atccagaagt cagattaata atgaaagtaa atacctctcc ttcagcagga      5100
tatatacggt tttataatga atttgctaaa agacctatta tgtacttgaa ttatgtttat      5160
actaaggcag aagttaagtt cactaacact gaaaaattgc taactactat acataaaggg      5220
ttaattagag ccttagatct tgccatggga caagaaatct tagtatatag tcctatcgta      5280
tccatgacca aaattcaaaa aacaccatta ccagaaagaa aagctctacc aattagatgg      5340
ataacctgga tgtcttattt agaagatccc agaatacaat ttcattatga taagacatta      5400
cccgagctac aacaggttcc tactgtcact gatgatgtta tagctaagac taaacatcct      5460
agtgaattta atatggtctt ctacactgat ggttctgcaa tcagacatcc aaatgttaat      5520
aagtcacata gtgctggaat gggtattgct caagtacagt ttaaacctga gtttacagtt      5580
gttaatactt ggtctattcc tcttggagat catacggcac aacttgccga agttgcagct      5640
gtagaatttg catgtaaaaa ggccctcaaa atagatggac ctgttttaat agtaactgat      5700
agtttctatg ttgctgagag tgctaataag gaattaccyt attggcaatc aaatgggttc      5760
tttaataaca aaaagaaacc ccttaaacat gtctccaagt ggaagtcaat tgcagaatgt      5820
gtacaattaa agcctgacat tactattatt catgaaaaag gtcaccagcc tactgcttca      5880
acatttcata cagaaggtaa taatttagct gataagcttg ccacccaagg aagttatgtg      5940
gtaaatacaa ataccactcc aagcctggat gcagagttgg atcaattact acaaggacaa      6000
tatccaaaag gttttccaaa acaatatcaa tatgaactta atgaaggaca agttatagta      6060
actcgtccta atggacaaag aattattcct ccaaaatcag acaggcctca aattattttg      6120
caagcacata atattgcaca tacaggaaga gattcaacct ttcttaaggt ctcttccaag      6180
tattggtggc aaatcttag aaaggatgtg gttaaagtta tcagacaatg taagcaatgt      6240
ctggtcacaa atgcagctac cttagctgcg cctccaatac tgaggcctga agacctgta       6300 aagccttttg ataaatttt tgttgactat attggcccctt tacccccttc taatrggtac      6360
ttacatgtcc ttgtagtagt cgatggtatg actggatttg tatggttata ccccactaag      6420
gctccttcaa ctggcgcaac tgttaaagct ctcaatatgc tcactagtat tgcagttcca      6480
aaggtgatac actctgatca gggtacagca ttcacctctg caacttttgc tgattgggca      6540
aaagacaaag gtacacattt ggaattcagt actccttacc atccccaaag tagtggcaag      6600
gtggaaagga aaaatagtga tataaaacga cttttaacta aactgcttgg tgggagacct      6660
gctaagtggn atgaccttct ttcagttgtt caattggcat taaataattc atataggcct      6720 cttttcttcta aatatactcc tcatcaactt ttgtttggta tagattcaaa tacaccattt      6780
gcaaactctg atacacttga tttatcaaga gaagaagaac tctctctttt acaggaaatc      6840
agaacttctc tttgccatcc atcctcccct cctgcctccg ttcgtgtctg gtctccttct      6900
gttggccaat tggtccagga gagggtagcc aggcctgcat ctttaagacc tcggtggcat      6960
aaacctactc ctgttctgga agtcattaat ccacgaactg ttgtcatttt ggaccatctt      7020
ggcaacagga gaactgtaag tgtggataat ttaaaattaa carcttatca gaaggatggc      7080
acctccaatg aatctgcagc aatggctatt gtggaaaaag atgaatgaag cacattcagc      7140
gttagagaat atttcaaccc ttactgaaga acagaagcaa caagtgatta ttgagattca      7200
acaagaagaa gtaataccta ctaggatgga cagagtaaag tatctagcat atgcatgttg      7260
tgctaccagt acacgtgtca tgtgttggtt atttttgatt tgtgtgttgc taattattgt      7320
atttgtatct tgttttgtca ctgttgctag gattcaatgg aataaggata ttactgtgtt      7380
```

```
tggaccagtc attgattgga atgttaccca tcaagcaaca tatcaacagc ttagagcttc    7440
cagaatagct agatctttaa gggtagaaca tcctcatata tcatatatat caataaatat    7500
gtctagtata ccacaaggtg ttatatatac acctcaccct gaacctataa tcctcaagga    7560
gagggtttta gggatttctc agtgttaat gataaattct gaaaatatag ctaatgtggc     7620
caatttgtct caagcacaa aagtattgtt gactgatatg ataaatgagg aattacaaga     7680
tttgtcaaac caaatgattg acttcgaatt acctctagga gatcctagag accaaaatca    7740
atatgtacat cataagtgtt accaggagtt tgctcattgt tatttagtca aatataaaac    7800
acntaaagaa tggccctctt cagctctgat tgctgatcag tgtcccctac caggagaaca    7860
tccaactgta cagtattcac atcaaaatat atgggactat tatgttcctt ttcaacaaat    7920
acggccagag aaatggactt catccttagt atatgaagat gctagaatag ggagcttcta    7980
tataccaaaa aatatgagaa acaagaatgt tacacatgta atattttgtt cagatcaatt    8040
atatggaaaa tggtataatt tgatgaatac tgtacaagaa aatgaacaaa ttcaagtcat    8100
aaaattaaaa aatattacca atcgggtac ctctcaagtt aaggatagag gacttccgtc     8160
cgcttggcat aagaatggta aaagtacata ttttaggcct attaatactt tggatatttg    8220
taatagacct gagttagtat tattactcaa tagtacttat tatactctct ctctgtggga    8280
aggagattgt ggatatacta gggaaaatgc tactcaagct aatcctcttt gtaaaaactt    8340
ttataatgaa tctaaaaaac attggcaccc atacgcatgt aggttttgga gatataaaaa    8400
tgataaagaa gaggttaagt gtagaaatga ggataaaaaa cactgtattt attatcccct    8460
ttgggatacc ccggaagcct tatatgattt tggatttttg gcatatctta atgcattccc    8520
ttcaccactt tgtattacaa atcaaactgt taggagcca gagtatgaag tatattcctt     8580
atatatggaa tgtatgaatt ctgcggaaaa atatggaata gatagtgttt tgtttgcttt    8640
aaaaactttt ttaaatttta ctggaacacc agtgaatgaa atgccaacag ccagagcatt    8700
tgtaggcctg actgatccta aattccctcc agtatatcca aatattacta agaacgaag     8760 aggatgtgac aattcaagaa ggaaaagaag aagcactaat attgaaaaac ttaggtcaat    8820
gggatactca ttgactggag ctgtgcagac cctctcacaa atatcagata taaatgatga    8880
aagacttcaa caaggagttt acttattgag agatcatgtt gtcaccttaa tggaagccgc    8940
cttgcatgat attactatta tggaaggaat gttagcaatc ggtcatgtgc atacccactt    9000
gaatcatctt aaaaccatgt tactaatgag gaagattgac tggactttta ttaagagtga    9060
ttggattaaa gaacaacttc agaaaactga agatgaaatg aagattatta gaagaacagc    9120
taaaagttta gtatattatg tgactcaaac atcatcttcc actacagcaa catcatggga    9180
aattggaatt tattatgaaa taactatacc aaaacatatt tatttgaata attggcaagt    9240
tgttaacata ggtcatctga ttgagtcagc tggtcatttg accttaataa gggttaaaca    9300
tccttatgaa gactttaata aagaatgcac atatgaacaa tatttacatc ttgaagactg    9360
catatctcag gattatgtga tttgtgacac ggtacaaata gtgtcaccat gtggaaactc    9420
aacagtaacc agtgactgcc ctgtcactgc tgaaaaggta aaggaaccat atattcaagt    9480
gtcagcttta aaaatggaa gctatttggt tctaaccagt agaacagatt gctcaatacc     9540
agcatatgtt cccagcattg taactgtgaa cgaaacagtt aagtgttttg gggttgagtt    9600
tcataaacca ctatactcag aaagtaaagt cagctttgaa ccacaagttc cacatctgaa    9660
actacgcttg ccacatctgg ttgggattat tgcaagtctt caaaatttgg aaattgaagt    9720
aaccagcacc caagagagta taaaagatca gattgaaaga gttcaatcac agcttcttcg    9780
```

-continued

```
gctggacatt cacgagggag actttcctgc ttggattcaa caacttgctt ctgcaaccaa    9840
ggacgtctgg cctgcagctg ctaaagctct tcaaggcata ggtaactttt tatctaatac    9900
tgcccaggga atatttggaa ctgctgtaag tattctatcc tatgccaagc ctattcttat    9960
aggaataggt gttatacttt tgattgcatt cttgtttaag attgtatcat ggcttcctgg   10020
gaagaagaaa aagaactagg acatctgcat cttccagaag acgatcctct gcccaattta   10080
gatgtgctcc tgggtcttga tcatatggaa tccaatgaag acctgatca aaatccagga   10140
gctgaaaaga tctacattca actccaagca gtcccagggg aagcctcaga gaaaacttac   10200
aaatttggat atgaagacaa agaggcacaa aatcctgact taaaaatgag aaattgggtt   10260
cctaaccccg acaaaatgag taagtgggcc tgtgcaaggc ttattctttg tggactttat   10320
aatgcaaaaa aggctggaga actcttggct atggactata atgttcaatg gaacaatca    10380
aaagaagacc caggatactt tgaagtggaa tatcactgta aaatgtgcat gactgttatt   10440
catgaaccta tgcctatcca atatgatgaa aaaactggat tatggctaaa aatgggtccc   10500
cttaggggag atataggatc tgtagtacat acttgtagaa ggcattacat gagatgtttg   10560
tctgcccttc ctagcaatgg agaacctctc aaacctagag tccggctaa tcctgtccga    10620
agatatcgag agaagcaaga gttcgttgcg actaggccta aacgctccag atggggtgtg   10680
gccctagcg cagactccca tacttccagt ggtgacgcca tggcccttat gccaggacca    10740
tgcggccccc tcggtatgga cactcctggt tgcttactgg aagggataca aggatcaggg   10800
cctgaaacct ccgaaatggc tgtggcaatg tcaggaggac ctttctggga agaagtgtat   10860
cgagactcaa ttcttggtgc ccccactggg tctagtgaaa attaggcttt atcaaaatct   10920
aactgttgta aatgtttgtg gatctgttga cccatgggaa aatgagaatc ccactagagg   10980
tcgcagaggg cctatgcata gatatgattg tagaattgct tgtgatccaa gctattgctt   11040
taaggctatt tgggaaggaa acttttggga caaaaaaaaa aggatcaggc atgctggcta   11100
gttcatctga aagaaggaca taaatttggt gcagatgagt tatcttctgg ggatcttaaa   11160
atattagcag aatctagacc ttatccatat ggatctattg gtcattgtgc tatgcttcaa   11220
tatgcagtac aagttaaaat gagagttgat agagctcctt tgacctcaaa ggtgagagct   11280
attaaagctt tgcactatca tcgctggaat atttgtcagc tggaaaatcc tggcatagga   11340
gagggattca gtccctctgg taatacacaa gctcttaaag cctatggacc tcagcatgga   11400
agtgaagagg agagggtgtg gctgacagct actaaaatga ttggcaccca ggaatcagac   11460
tattggcatg agtacaaaag atggggatat ttccctttga ttccaaataa acatcatcct   11520
gggtggacta gacatcttac taaattcaag atatctagat tctccactcc tgctgatgtc   11580
cagaaaattg tggatgagct tctccctaga ggagcaagca ttgtaatgcc agatggaaca   11640
aagtatccaa gtaccagaaa agtgcactta gtcaatgaag gaaccttgt agaataccaa    11700
gccaaatgta aggagataga ggaaaagtac ggaggatgct tttctacaga tagtgatgat   11760
gacagtgatg attactctga ggatactcca gaaactgaaa ccactgatgt ggaatagagt   11820
acagtgttaa ggatttacat aatctgccta gcaactgctt atgcttaaga atgaatcagt   11880
atattgttta ggaataagcc ttagtttata agtagttaat ccttagggag tatttggtgg   11940
aaatgactga gtgacatgaa gtttattcac catactctca ataggagcca ctagttgagc   12000
ctgtgcgttc aaatccatgc tcagcttaag tgactccctt ttagtttcac tttaagttaa   12060
gttaggaata agttccatat aatcctaagg gagtatgtgg accttcttgt taggaaatag   12120
```

-continued

```
tttaagatag tccacagctc ccttcttttt gagttctagt ctttgttaag tttgttggct  12180
catacagata aagtgctcat taaacaggaa accgcaaccg ggtaaaggtt agcacagtaa  12240
attaagctag cagttactca agagcccggt aagcattcaa gtagttcgaa tccctttaat  12300
gctgacggat tgctctttag tgaggtgatg taatctgttt ttgcaatctg aaatgtgtgt  12360
ttgcacagga agttgtacaa gaaagggaat ggctaaactt gttacagttc gaacaaacat  12420
ttagcaattt cctttgcttt tggagttcga gccttgtact tatactttga gcatatgtat  12480
tgtaacacct aagtatggaa aaatctccaa gtatgagtca cgagatgctt ggctcactgc  12540
gttggacgac tggaaagaag cttcaacagt cgggacagca tctcgaagaa ggcctccgga  12600
atgaaagagt gaaaaatgaa gtctcctcat tcagagagcc ttcttttaga atttcaggca  12660
gaatagagtt tccaatagaa taaacttttg tattagcaga tagataggat atataatctc  12720
tgctttagat tgtacgggag ctcaccacta ctcgctgcgt cgagagtgtt cgagtctctc  12780
caggcttggt aagatataaa ctttggtatt ctctgtattc ttatgatcca atattactct  12840
gcttatagat tgtaatgggc aatggcaatg ctttatcaat gaatgatttt atggtgaatt  12900
aagttcatat atgttttaag aagtttaaca ataaaccgac ttaattcgag aaccagattt  12960
attagtattg tctctttcta tactttaagt aaagtgaaag gagttgtata ttagccttgc  13020
ttataagagc catctagtgg tataagtgtg tactacactt atctaaa                13067
```

What is claimed:

1. A method for detecting a spumavirus infection, comprising, contacting a sample of nucleic acids with a probe comprising a sequence specific for SFVHu-1.

2. The method of claim 1, wherein the probe sequence comprises a fragment of SEQ ID NO. 1, wherein the fragment is specific for SEQ ID NO. 1.

3. The method of claim 1, wherein the probe sequence comprises a fragment of SEQ ID NO. 2, wherein the fragment is specific for SEQ ID NO. 2.

4. The method of claim 1, wherein the probe sequence comprises a fragment of SEQ ID NO. 3, wherein the fragment is specific for SEQ ID NO. 3.

5. The method of claim 1, wherein the probe sequence comprises a fragment of SEQ ID NO. 4, wherein the fragment is specific for SEQ ID NO. 4.

6. The method of claim 1, wherein the probe sequence comprises a fragment of SEQ ID NO. 5, wherein the fragment is specific for SEQ ID NO. 5.

7. The method of claim 1, wherein the probe sequence consists of a fragment of SEQ ID NO. 1, wherein the fragment is specific for SEQ ID NO. 1.

8. The method of claim 1, wherein the probe sequence consists of a fragment of SEQ ID NO. 2, wherein the fragment is specific for SEQ ID NO. 2.

9. The method of claim 1, wherein the probe sequence consists of a fragment of SEQ ID NO. 3, wherein the fragment is specific for SEQ ID NO. 3.

10. The method of claim 1, wherein the probe sequence consists of a fragment of SEQ ID NO. 4, wherein the fragment is specific for SEQ ID NO. 4.

11. The method of claim 1, wherein the probe sequence consists of a fragment of SEQ ID NO. 5, wherein the fragment is specific for SEQ ID NO. 5.

12. A method for detecting a spumavirus infection, comprising, contacting a sample of nucleic acids with a probe comprising a sequence of SFVHu-1, wherein the sequence is specific for a virus which comprises a polymerase gene with greater than 87.5% sequence identity to the polymerase gene of SFVHu-1.

13. A method for detecting a spumavirus infection, comprising, contacting a sample of nucleic acids with a probe comprising a sequence of SFVHu-1, wherein the probe does not consist of a sequence of SFV-3.

14. The method of claim 1, wherein the probe sequence comprises SEQ ID NO. 1.

15. The method of claim 1, wherein the probe sequence comprises SEQ ID NO. 2.

16. The method of claim 1, wherein the probe sequence comprises SEQ ID NO. 3.

17. The method of claim 1, wherein the probe sequence comprises SEQ ID NO. 4.

18. The method of claim 1, wherein the probe sequence comprises SEQ ID NO. 5.

* * * * *